United States Patent
Wu et al.

(10) Patent No.: US 8,632,828 B2
(45) Date of Patent: Jan. 21, 2014

(54) CHINESE HERBAL MEDICINE COMPOSITION USED FOR ANTIINFLAMMATION, DETUMESCENCE AND ACESODYNE, AND PREPARATION METHOD AND USE THEREOF

(75) Inventors: Tian Shung Wu, Tainan (TW); Tai-Ting Chou, Tainan (TW)

(73) Assignee: Uni-President Biotech Co., Ltd., Tainan (TW)

( * ) Notice: Subject to any disclaimer, the term of this patent is extended or adjusted under 35 U.S.C. 154(b) by 0 days.

(21) Appl. No.: 13/393,559

(22) PCT Filed: Sep. 1, 2009

(86) PCT No.: PCT/CN2009/073664
§ 371 (c)(1),
(2), (4) Date: Mar. 1, 2012

(87) PCT Pub. No.: WO2011/026267
PCT Pub. Date: Mar. 10, 2011

(65) Prior Publication Data
US 2012/0164249 A1    Jun. 28, 2012

(51) Int. Cl.
| A61K 36/00 | (2006.01) |
| A61K 36/232 | (2006.01) |
| A61K 36/237 | (2006.01) |
| A61K 36/236 | (2006.01) |
| A61K 36/708 | (2006.01) |
| A61K 36/268 | (2006.01) |
| A61K 36/328 | (2006.01) |

(52) U.S. Cl.
USPC ........... 424/725; 424/756; 424/773; 424/775; 424/757; 424/748

(58) Field of Classification Search
None
See application file for complete search history.

(56) References Cited

U.S. PATENT DOCUMENTS 6,607,756 B1 *   8/2003   Rosenstiel .................... 424/748

FOREIGN PATENT DOCUMENTS

| CN | 2216416 Y | 1/1996 |
| CN | 1273837 A | 11/2000 |
| CN | 1401360 A | 3/2003 |
| CN | 101002900 A | 7/2007 |
| KR | 2009021644 A | * 3/2009 |

OTHER PUBLICATIONS

International Search Report for PCT/CN2009/073664 dated May 27, 2010.

* cited by examiner

Primary Examiner — Qiuwen Mi

(57) ABSTRACT

A Chinese herbal medicine composition used for antiinflammation, detumescence and acesodyne, comprising first type medicinal material and second type medicinal material. The first type medicinal material includes Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei. The second type medicinal material includes one, two, or three selected from the group consisting of *Zingiber Officinale, Olibanum,* and *Myrrha*. The preparation method for the Chinese herbal medicine composition includes adding the first type medicinal material and the second type medicinal material into a container with organic solvent, heating, filtering, and then condensing the filtrate into an extractum.

16 Claims, 11 Drawing Sheets

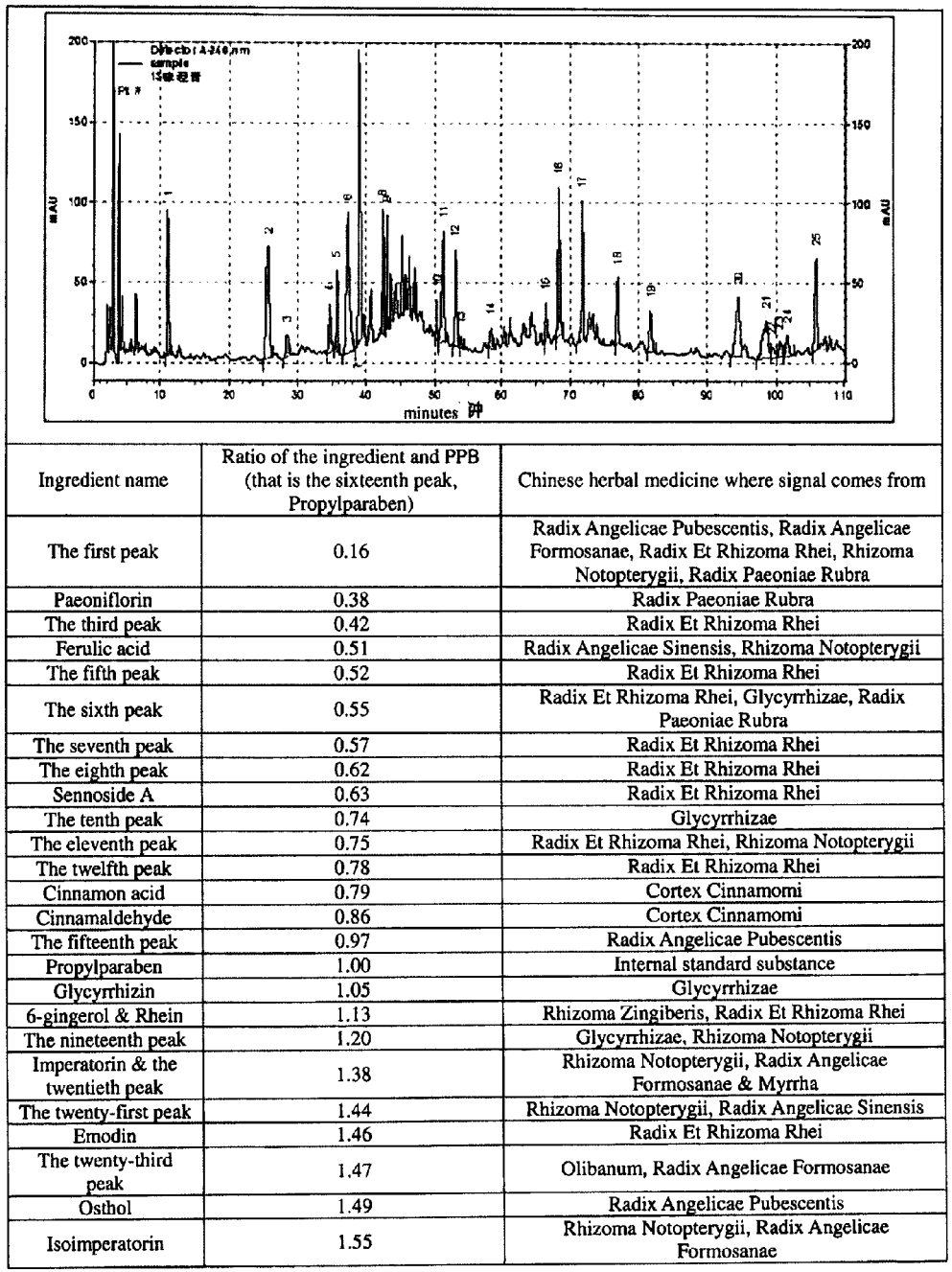

| Ingredient name | Ratio of the ingredient and PPB (that is the sixteenth peak, Propylparaben) | Chinese herbal medicine where signal comes from |
|---|---|---|
| The first peak | 0.16 | Radix Angelicae Pubescentis, Radix Angelicae Formosanae, Radix Et Rhizoma Rhei, Rhizoma Notopterygii, Radix Paeoniae Rubra |
| Paeoniflorin | 0.38 | Radix Paeoniae Rubra |
| The third peak | 0.42 | Radix Et Rhizoma Rhei |
| Ferulic acid | 0.51 | Radix Angelicae Sinensis, Rhizoma Notopterygii |
| The fifth peak | 0.52 | Radix Et Rhizoma Rhei |
| The sixth peak | 0.55 | Radix Et Rhizoma Rhei, Glycyrrhizae, Radix Paeoniae Rubra |
| The seventh peak | 0.57 | Radix Et Rhizoma Rhei |
| The eighth peak | 0.62 | Radix Et Rhizoma Rhei |
| Sennoside A | 0.63 | Radix Et Rhizoma Rhei |
| The tenth peak | 0.74 | Glycyrrhizae |
| The eleventh peak | 0.75 | Radix Et Rhizoma Rhei, Rhizoma Notopterygii |
| The twelfth peak | 0.78 | Radix Et Rhizoma Rhei |
| Cinnamon acid | 0.79 | Cortex Cinnamomi |
| Cinnamaldehyde | 0.86 | Cortex Cinnamomi |
| The fifteenth peak | 0.97 | Radix Angelicae Pubescentis |
| Propylparaben | 1.00 | Internal standard substance |
| Glycyrrhizin | 1.05 | Glycyrrhizae |
| 6-gingerol & Rhein | 1.13 | Rhizoma Zingiberis, Radix Et Rhizoma Rhei |
| The nineteenth peak | 1.20 | Glycyrrhizae, Rhizoma Notopterygii |
| Imperatorin & the twentieth peak | 1.38 | Rhizoma Notopterygii, Radix Angelicae Formosanae & Myrrha |
| The twenty-first peak | 1.44 | Rhizoma Notopterygii, Radix Angelicae Sinensis |
| Emodin | 1.46 | Radix Et Rhizoma Rhei |
| The twenty-third peak | 1.47 | Olibanum, Radix Angelicae Formosanae |
| Osthol | 1.49 | Radix Angelicae Pubescentis |
| Isoimperatorin | 1.55 | Rhizoma Notopterygii, Radix Angelicae Formosanae |

FIGURE 7

CHINESE HERBAL MEDICINE COMPOSITION USED FOR ANTIINFLAMMATION, DETUMESCENCE AND ACESODYNE, AND PREPARATION METHOD AND USE THEREOF

RELATED APPLICATIONS

The present application is a National Phase of International Application PCT/CN2009/073664, filed Sep. 1, 2009.

FIELD OF THE INVENTION

The invention relates a Chinese herbal medicine composition used for antiinflammation, detumescence and acesodyne; and more specifically, to a Chinese herbal medicine extractive used for antiinflammation, detumescence and acesodyne and a preparation method and use thereof

BACKGROUND OF THE INVENTION

The life of modern people has become more and more stress and busy, they have not much time to do exercises, and they always stand or sit, thus modern people often have many civilization diseases, such as nerve or bones and muscles inflammation, muscle ache and so on. If lacking treatment, the result is that vicious circle forms, qi and blood can not circulate smoothly.

From the earliest times, it has been several thousand years since Chinese people used Chinese herbal medicine to treat diseases. All the time, they apply the method of consolidating the constitution and resisting the pathogen to cure foreign diseases, and solve the intrinsic inflammation or ache, which make Chinese herbal medicine continue today.

At present, workers in Chinese herbal medicine industry still develop Chinese herbal medicine patch. The Chinese herbal medicine patch is convenient for external use, what is needed is only to place Chinese herbal medicine patch on the skin of area which suffers from pain or discomfort, and efficacy can work by making the ingredients in Chinese herbal medicine patch penetrate into the skin of body.

Panchrest plaster has been used for curing the symptoms of body ache and discomfort etc. since ancient times, therefore efficacy has been confirmed for a long time, the formula is composed of 17 kinds of medicinal materials, such as Radix Aconiti, Momordica Cochinchinensis, Radix Aconiti Kusnezoffii, Radix Rehmanniae, Ampelopsis Japonica, Rhizoma Bletillae, Cortex Cinnamon, Radix Angelicae Formosanae, Radix Angelicae Sinensis, Radix Paeoniae Rubra, Rhizoma Notopterygii, Radix Sophorae Flavescentis, Radix Linderae, Glycyrrhiza, Radix Angelicae Pubescentis, Radix Scrophulariae, Radix Et Rhizoma Rhei. However, a part of medicinal materials in the above formula, such as Radix Aconiti, Momordica Cochinchinensis, Radix Aconiti Kusnezoffii, have been verified to be toxic and have dermal irritation, which may cause skin discomfort after using, as showed in Table 1.

TABLE 1

Medicinal materials: Efficacy and defects of Radix Aconiti, *Momordica Cochinchinensis* and Radix Aconiti Kusnezoffii

| Medicinal materials | Medicine properties | Efficacy and defects |
|---|---|---|
| Radix Aconiti | Medicine properties: acrid and bitter in taste, hot in nature, extremely poisonous<br>1. *Aconitum Carmichaelii* in "Wu Pu's Meteria Medica", Shen Nong, Lei Gong, Tong Jun, Yellow Emperor: was sweet, poisonous.<br>2. *Aconitum Carmichaelii* in "Bie Lu", was sweet, graet heat, extremely poisonous<br>3. In "Yao Xing Lun", was bitter, acrid, great heat, extremely poisonous<br>4. In "Zhen Zhu Nang Bu Yi Yao Xing Fu", was acrid and bitter, hot in nature, extremely poisonous, floating, yang within yang<br>Toxicity:<br>In "Chinese Materia Medica", mice was given Radix Aconiti apozem by gavage, LD50 was 18.0 ± 0.034 g/kg. People was given Aconitine by oral administration, fatal dosage was about 2~5 mg, LD50 by subcutaneous injection was 0.32 mg/kg for mice, mice was given mesaconitine by subcutaneous injection, fatal dosage was 0.3~0.5 mg/kg.<br>Cautions:<br>In "Chinese Materia Medica", Radix Aconiti soaked and decocted with wine may cause toxicity, people should be cautious. If it was used improperly to lead to poisoning, the symptom includes tongue, limbs and systematic numbness, salivation, nausea, vomit, diarrhea, dizziness, blur version, dry mouth, slow pulse, dyspnea, tetany, insanity, gatism, blood pressure and temperature dropped. One with severe poisoning might die resulted from the respiratory and circulatory failure and severe cardiac arrhythmia. | Radix Aconiti had obvious effect on antiinflammation and acesodyne, but has toxicity |
| *Momordica Cochinchinensis* | Medicine properties: bitter and slightly sweet in taste, warm in nature, poisonous<br>1. In "Wang Mu", bitter and slightly sweet in taste, mildly poisonous<br>2. In "Yao Xing Qie Yong", bitter in taste, great cold in nature<br>3. In "Yao Xing Kao", mildly poisonous, cool<br>Cautions: pregnant woman and persons with body weakness must not take in. | *Momordica Cochinchinensis* has effect on detumescence and lump dissipation, detoxication, chasing wind and pain-alleviating, but |

TABLE 1-continued

Medicinal materials: Efficacy and defects of Radix Aconiti, *Momordica Cochinchinensis* and Radix Aconiti Kusnezoffii

| Medicinal materials | Medicine properties | Efficacy and defects |
|---|---|---|
| | 1. In "Collected Works of Materia Medica", people with stomach deficiency, whose large intestine is not material and true origin has no damage, can not use.<br>2. In "Sheng Cao Yao Xing Bei Yao", fishy in taste, poisonous, can not be taken in. | had high irritation |
| Radix Aconiti Kusnezoffii | Medicine properties: acrid and bitter in taste, hot in nature, extremely poisonous<br>1. *Aconitum Carmichaelii* in "Wu Pu's Meteria Madica", Shen Nong, Lei Gong, Tong Jun, Yellow Emperor: was sweet, poisonous.<br>2. *Aconitum Carmichaelii* in "Bie Lu", was sweet, great heat, extremely poisonous<br>3. In "Yao Xing Lun", was bitter, acrid, great heat, extremely poisonous<br>4. In "Xin Xiu Ben Cao", acrid sweet, warm in taste, great hot, extremely poisonous<br>Toxicity:<br>In "Chinese Materia Medica", mice was given with *Aconitum Carmichaelii* (Radix Aconiti Kusnezoffii) extract by oral administration, LD50 (dried herb) was 1827 ± 11.4 mg/kg, 5780 ± 4.4 mg/kg for *Aconitum Kusnezoffii*. LD50 of *Aconitum Carmichaelii* by intraperitoneal injection was 1.62 ± 1.1 mg/kg, 435 ± 4.4 mg/kg for *Aconitum Kusnezoffii*.<br>Cautions:<br>In "Chinese Materia Medica", Radix Aconiti soaked and decocted with wine may cause toxicity, people should be cautious. Excessive dosage might cause toxicity, poisoning symptom might refer to "Radix Aconiti". | Radix Aconiti Kusnezoffii has obvious effect on antiinflammation and acesodyne, but has toxicity |

Additionally, Panchrest plaster from ancient formula mainly applies oleum sesami to extract the effective ingredients, which can destroy the ingredients in medicinal materials because of high temperature, or lead to the incomplete extraction of the effective ingredients, it is not easy to manage and when molding, due to add lots of zinc oxide, the problem of heavy metal residue is caused.

Therefore, it is necessary to provide a Chinese herbal medicine composition used for antiinflammation, detumescence and acesodyne, so as to solve the above problems.

SUMMARY OF THE INVENTION

The present invention provides a Chinese herbal medicine composition used for antiinflammation, detumescence and acesodyne, comprising a first type of medicinal materials and a second type of medicinal materials, wherein the first type of medicinal materials include Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei, the second type of medicinal materials is one, two or three selected from the group consisting of *Zingiber Officinale, Olibanum* and *Myrrha*.

The present invention further provides a Chinese herbal medicine extractive, prepared by a process comprising the following steps: providing a first type of medicinal materials and a second type of medicinal materials, wherein the first type of medicinal materials include Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei, which are basic medicinal materials, and the second type of medicinal materials is one, two or three selected from the group consisting of *Zingiber Officinale, Olibanum* and *Myrrha*, which are added medicinal materials; adding the first type of medicinal materials and the second type of medicinal materials into a container with organic solvent, making the percent by weight of the first and second type of medicinal materials with the organic solvent reach 1:N, so as to form a first mixed solution, wherein N is a number between 3 and 12; heating the first mixed solution to a first predetermined temperature and performing the extraction for a first predetermined time, so as to carry out first extraction, filtering the first mixed solution while hot, to achieve filtrate from the first extraction.

The present invention further provides a preparation method of a Chinese herbal medicine extractive, wherein the preparation method comprises the following steps: providing a first type of medicinal materials and a second type of medicinal materials, wherein the first type of medicinal materials include Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei, which are basic medicinal materials, and the second type of medicinal materials is one, two or three selected from the group consisting of *Zingiber Officinale, Olibanum* and *Myrrha*, which are added medicinal materials; adding the first and second type of medicinal materials into a container with organic solvent, making the percent by weight of the first and second type of medicinal materials with the organic solvent reach 1:N, so as to form a first mixed solution, wherein N is a number between 3 and 12; heating the first mixed solution to a first predetermined temperature and performing the extraction for a first predetermined time, so as to carry out a first extraction, filtering the first mixed solution while hot achieving a filtrate from the first extraction.

The present invention further provides an use of the Chinese herbal medicine composition, for example, the Chinese herbal medicine composition is used for Chinese herbal medicine patch, Chinese herbal medicine paste and oral preparation.

The present invention provides a Chinese herbal medicine composition used for antiinflammation, detumescence and acesodyne, which does not comprise Radix Aconiti, Momordica Cochinchinensis, Radix Aconiti Kusnezoffii, Radix Rehmanniae, Ampelopsis Japonica, Radix Sophorae Flavescentis, Radix Scrophulariae. Thus, the Chinese herbal medicine composition used for antiinflammation, detumescence and acesodyne according to the present invention, is completely different from original formula of panchrest plaster. Moreover, it has been verified that Radix Aconiti, Momordica Cochinchinensis, Radix Aconiti Kusnezoffii have toxicity and dermal irritation; therefore, the Chinese herbal medicine composition according to the present invention does not have defects which original formula of panchrest plaster has. Additionally, compared with original formula of panchrest plaster, the Chinese herbal medicine composition according to the present invention further comprises the added medicinal materials (such as *Zingiber Officinale, Olibanum* and *Myrrha*) so as to enhance efficacy.

The present invention chooses effective Chinese herbal medicine which has no irritation and anaphylaxis on skin and body, and applies special extraction and preparation method and animal test methods to verify the efficacy of antiinflammation, detumescence and acesodyne, which is different from the traditional panchrest plaster and commercial Chinese herbal medicine patch. The invention is illustrated in detail combined with figures below.

BRIEF DESCRIPTION OF THE DRAWINGS

FIG. 7 is a fingerprint for the Chinese herbal medicine composition according to the present invention analyzed by HPLC.

DETAILED DESCRIPTION OF THE EMBODIMENTS

Figure 1:
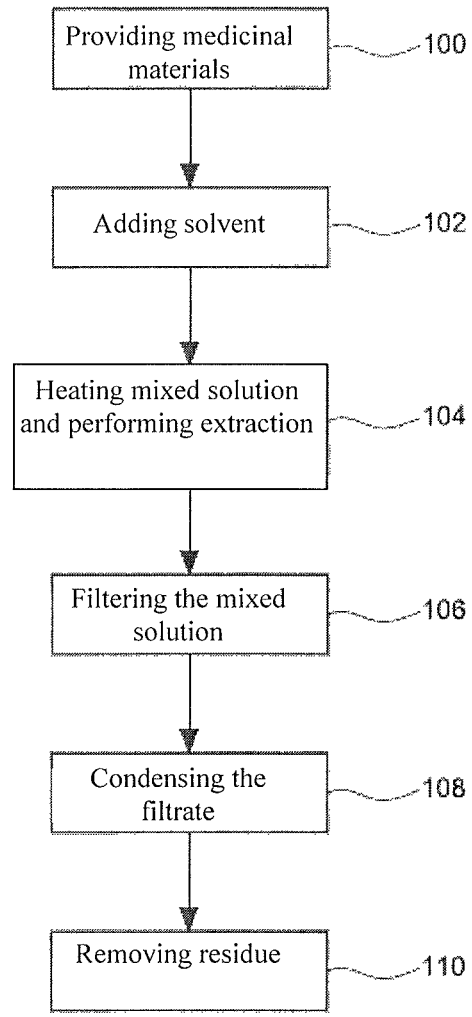
FIG. 1 is a flow chart for illustrating the first embodiment of the preparation method according to the present invention.

The invention provides a Chinese herbal medicine composition; the composition comprises a first type of medicinal materials and a second type of medicinal materials. Wherein, the first type of medicinal materials include Rhizoma Bletillae, Cortex Cinnamomi, Radix Angelicae Formosanae, Radix Angelicae Sinensis, Paeonia Lactiflora (such as Radix Paeoniae Rubra), Rhizoma Notopterygii, Radix Linderae, Glycyrrhizae, Radix Angelicae Pubescentis, and Radix Et Rhizoma Rhei, which are basic medicinal materials. The second type of medicinal materials is one, two or three selected from the group consisting of *Zingiber Officinale, Olibanum* and *Myrrha*, which are added medicinal materials. Specifically, the Chinese herbal medicine composition according to the present invention includes seven kinds of combinations of medicinal materials as shown in Table 2.

TABLE 2

| | Medicinal materials of the invention Basic medicinal materials | | | | | | |
|---|---|---|---|---|---|---|---|
| | Rhizoma Bletillae | Cortex Cinnamomi | Radix Angelicae Formosanae | Radix Angelicae *Sinensis* | *Paeonia Lactiflora* | Rhizoma Notopterygii | Radix Linderae |
| There are 11 kinds in the first combination | Yes | Yes | Yes | Yes | Yes | Yes | Yes |
| There are 11 kinds in the second combination | Yes | Yes | Yes | Yes | Yes | Yes | Yes |
| There are 11 kinds in the third | Yes | Yes | Yes | Yes | Yes | Yes | Yes |

TABLE 2-continued

| | | | | | | | |
|---|---|---|---|---|---|---|---|
| combination | | | | | | | |
| There are 12 kinds in the forth combination | Yes | Yes | Yes | Yes | Yes | Yes | Yes |
| There are 12 kinds in the fifth combination | Yes | Yes | Yes | Yes | Yes | Yes | Yes |
| There are 12 kinds in the sixth combination | Yes | Yes | Yes | Yes | Yes | Yes | Yes |
| There are 13 kinds in the seventh combination | Yes | Yes | Yes | Yes | Yes | Yes | Yes |

| | Medicinal materials of the invention | | | | | |
|---|---|---|---|---|---|---|
| | Basic medicinal materials | | | Added medicinal materials | | |
| | *Glycyrrhizae* | Radix Angelicae Pubescentis | Radix Et Rhizoma Rhei | *Zingiber Officinale* | Olibanum | *Myrrha* |
| There are 11 kinds in the first combination | Yes | Yes | Yes | Yes | None | None |
| There are 11 kinds in the second combination | Yes | Yes | Yes | None | Yes | None |
| There are 11 kinds in the third combination | Yes | Yes | Yes | None | None | Yes |
| There are 12 kinds in the forth combination | Yes | Yes | Yes | Yes | Yes | None |
| There are 12 kinds in the fifth combination | Yes | Yes | Yes | Yes | None | Yes |
| There are 12 kinds in the sixth combination | Yes | Yes | Yes | None | Yes | Yes |
| There are 13 kinds in the seventh combination | Yes | Yes | Yes | Yes | Yes | Yes |

When the second type of medicinal materials is one selected from the group consisting of *Zingiber Officinale, Olibanum* and *Myrrha*, the Chinese herbal medicine composition contains 11 kinds of medicinal materials, percent by weight of each medicinal material is in the range of 9.09%±5%. When the second type of medicinal materials is two selected from the group consisting of *Zingiber Officinale, Olibanum* and *Myrrha*, the Chinese herbal medicine composition contains 12 kinds of medicinal materials, percent by weight of each medicinal material is in the range of 8.33%±5%. When the second type of medicinal materials is three selected from the group consisting of *Zingiber Officinale, Olibanum* and *Myrrha*, the Chinese herbal medicine composition contains 13 kinds of medicinal materials, percent by weight of each medicinal material is in the range of 7.69%±5%.

In the present invention, the first type of medicinal materials is basic medicinal materials, and the second type of medicinal materials is added medicinal materials. 7 kinds of combinations of medicinal materials in Table 2 all have efficacy of the invention. In the context below, only take the seventh combination for example, which comprises 13 kinds of medicinal materials in the Chinese herbal medicine composition (that is, Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, Radix Et Rhizoma Rhei, *Zingiber Officinale, Olibanum* and *Myrrha*), the other 6 combinations can be carried out in the similar means, so it is not necessary to give more details here.

Table 3 shows the comparison between the formula of the Chinese herbal medicine composition used for antiinflammation, detumescence and acesodyne according to one embodiment of the present invention and original formula of panchrest plaster.

TABLE 3

| | Medicinal materials | | | | | | | | | |
|---|---|---|---|---|---|---|---|---|---|---|
| | Radix Aconiti | Momordica Cochinchinensis | Radix Aconiti Kusnezoffii | Radix Rehmanniae | Ampelopsis Japonica | Radix Sophorae Flavescentis | Rhizoma Bletillae | Rhizoma Bletillae | Cortex Cinnamomi | Radix Angelicae Sinensis |
| Formula of panchrest plaster | Yes | Yes | Yes | Yes | Yes | Yes | Yes | Yes | Yes | Yes |
| Formula of the present invention | None | None | None | None | None | None | None | Yes | Yes | Yes |

| | Medicinal materials | | | | | | | | | |
|---|---|---|---|---|---|---|---|---|---|---|
| | Radix Angelicae Sinensis | Paeonia Lactiflora | Rhizoma Notopterygii | Radix Linderae | Glycyrrhizae | Radix Angelicae Pubescentis | Radix Et Rhizoma Rhei | Zingiber Officinale | Olibanum | Myrrha |
| Formula of panchrest plaster | Yes | Yes | Yes | Yes | Yes | Yes | Yes | None | None | None |
| Formula of the present invention | Yes | Yes | Yes | Yes | Yes | Yes | Yes | Yes | Yes | Yes |

The Chinese herbal medicine composition used for antiinflammation, detumescence and acesodyne of the present invention does not comprise Radix Aconiti, Momordica Cochinchinensis, Radix Aconiti Kusnezoffii, Radix Rehmanniae, Ampelopsis Japonica, Radix Sophorae Flavescentis, Radix Scrophulariae. Thus, the Chinese herbal medicine composition used for antiinflammation, detumescence and acesodyne according to the present invention, is completely different from original formula of panchrest plaster. Moreover, it has been verified that Radix Aconiti, Momordica Cochinchinensis, Radix Aconiti Kusnezoffii have toxicity and dermal irritation; therefore, the Chinese herbal medicine composition according to the present invention does not have defects which original formula of panchrest plaster has. Additionally, compared with original formula of panchrest plaster, the Chinese herbal medicine composition according to the present invention further comprises the added medicinal materials (such as *Zingiber Officinale, Olibanum* and *Myrrha*) so as to enhance efficacy.

The Chinese herbal medicine composition used for antiinflammation, detumescence and acesodyne according to the present invention, the efficacy of medicinal materials recorded in the literature is shown in Table 4.

TABLE 4

| Medicinal materials | Characters and ingredients | Pharmacological action | Taste, nature and efficacy |
|---|---|---|---|
| Glycyrrhizae (Leguminosae sp.) Alias: sweet grass, sweet grass root, *Glycyrrhiza uralensis* Fisch Use part: rhizome, root | Characters The root is round in the form of long strip, no branches, 60.5-98.6 mm in length. As for one with bark, tightness of surface differs, wrinkle is obvious, the fibrous roots and scale leaves thereof is red brown, brown or grey brown; the texture thereof is solid, and the cutting surface on both ends is smooth, the section is fibroid, yellow white, mealiness, has obvious ring pattern and chrysanthemum core, has characteristic flavor, sweet in taste. As for one without bark, it is light yellow, appearance thereof is fibroid, cross section of rhizome has obvious cambium in two-thirds of radius, medulla is small in the center, xylem and phloem are radial, and section is fibroid. Ingredients Triterpenoids: | Immunoregulation, anticancer and anti-aging Glycyrrhizin: enhancing the weight of immune organs and raise the number of leucocyte. *Glycyrrhiza* polysaccharide: inducing r-interferon which has immunoregulation effect Glycyrrhizin: having immunoregulation effect and inhibiting or relieving the growth of tumour. *Glycyrrhiza* flavonoids: antioxidation, eliminating superoxide anion and hydroxy radical Treating ulcer and protecting liver, anticoagulation and reducing blood lipids Inhibiting gastric secretion, having the effect of ulcer resistance, enhancing pancreatic juice secretion. Protecting liver, reducing blood lipids, antiarrhythmic and inhibiting platelet | Sweet in taste, neutral in nature. Having the effect of invigorating spleen-stomach and replenishing qi, heat-clearing and etoxifying, expelling phlegm to stop cough, relieving spasm and pain, It is used for fatigue caused by qi deficiency, palpitation, and burnout, palpitation and severe palpitation, qi deficiency and blood less, knotted clavus, ulcer and swelling, sore throat, cough and much sputum, lung-heat and cough and panting, lung-cold and cough |

TABLE 4-continued

| Medicinal materials | Characters and ingredients | Pharmacological action | Taste, nature and efficacy |
| --- | --- | --- | --- |
| | 1. Glycyrrhetinic acid (Glycyrrhizin) Sweet ingredients in Glycyrrhizae 2. *Glycyrrhiza* saponins $A_3, A_2, C_2 \ldots$ 3. Flavonoid *Glycyrrhiza* flavonoids *Glycyrrhiza* Liquiritin and so on 4. Polysaccharide 5. Alkaloid | aggregation Antibacterial action and antitoxin High dosage of Glycyrrhizin can inhibit copy of SARS virus and has the effect of detoxication Antiinflammation and detumescence Glycyrrhetinic acid and derivative thereof can inhibit blood permeability of histamine, can be made into antiinflammation and antiallergic preparation used for rheumatic arthritis, allergic dermatitis and asthma Cosmetics Reducing or removing toxic substances in cosmetics, preventing allergic reaction on somebody, additionally, strongly inhibiting tyrosinase action | and panting, acute pain in the abdomen etc. It is also used for relieving medicine nature, gastric and duodenum ulcer, heat stranguria and dysuria, AIDS. |
| *Zingiber Officinale* (Zingiberaceae) Use part: dried rhizome | Characters Flat and in the form of irregular mass, having digitate branches. Length: 1-6 cm, thickness: 0.4-2 cm. Surface is gray or yellowish gray, rough, having longitudinal wrinkles and obvious rings, have scale leaves remaining in ramose place. Appearance of medicinal materials without bark is yellow white or light brown, smooth and have lognitudinal pinstripe. It is solid in texture, section is graininess, gray or light yellow, one with soft texture has visual venation, thin grease oil balls and obvious rings, aromatic in smell atmosphere, spicy in taste. Ingredients β-Pinene Myrcene γ-Selinene, Nonanol β-Sesquiphe-1 landrene Gingerol Zingiberone Zingerone Zonaren Shogaol | Sedation, acesodyne and antiinflammation Extracting solution from *zingiber Officinale* by methanol, can lengthen the sleeping time of anaesthetic mice, obviously inhibit writhing reaction reduced by acetic acid in mice, can also inhibit blood permeability caused by acetic acid, and treat rheumatic arthritis Effect on heart and blood *Zingiber Officinale* extractive can lead to transient rise of blood pressure in rats by intravenous injection. Effect on digestive system Water extractive from fresh *zingiber Officinale* can inhibit tonicity gastric ulcer and stimulate obviously and cause intestinal canal to contract Antihypoxic effect Ether exactive from *zingiber Officinale* can reduce amount of oxygen consumption in mice, and extend survival time after potassium hydroxide poisoning. | Bitter in taste, warm in nature, non-toxic. Function is warming the middle-Jiao mildly and removing cold, eliminating dampness and removing phlegm, stopping vomit and diarrhea, strengthening stomachic and analgesia, warming channels and stopping bleeding. It is mainly used for loin pain and blood stasis. |
| Olibanum (Burseraceae) Alias: Rushixiang, Taxiang, Tianjinxiang Use part: resin spilled from bark of lentisk | Characters: Lentisks are small shrubs, the trunk is thick and slippery, can be peeled off like paper. It is in the form of spherelike, guttate particle or irregular small mass, some is sticky and form mass, is light yellow, light blue-green or palm red, translucent. It is solid in texture, aromatic in smell, very bitter in taste, it becomes soft to be gum when chewing. Ingredients: resin 60~70% α-boswellic acid, β-boswellic acid, lactic acid resin hydrocarbon . . . gum 27~35% | Effect on treating stomach and duodenum ulcer Feeding rats for a long time, can redue obviously ulcer index and free acidity of gastric contents Antiinflammation Olibanoresin is an anti-inflammatory ingredient, can reduce glycosaminoglycan in skin, liver, kidney and spleen of rats after eating, which is related with anti-inflammatory effect. Reduce cholesterin Feeding rats can reduce the synthesis of cholesterin in liver. Acesodyne | Spicy and bitter in taste, warm in nature. Function includes activating blood analgesia, detumescence and promoting granulation. It is used for pain in the abdomen, Rheumatic arthralgia, physical injuries, line of abdominal pain, ulcer and swelling or slow-healing after ulceration etc. |

TABLE 4-continued

| Medicinal materials | Characters and ingredients | Pharmacological action | Taste, nature and efficacy |
|---|---|---|---|
| | Arab tanning polysaccharide acid<br>volatile oil 3~8%<br>amyrenone, pinocamphone, phellandral . . . | Olibanum has obvious acesodyne effect verified by writhing experiment induced by acetic acis | |
| Paeonia Lactiflora (Ranunculaceae) Alias: wood Paeonia lactiflora Use part: root | Character:<br>Root is cylindrical, slightly curved, 4-8.5 cm in length, about 9.1-11.1 mm in diameter, surface is dark brown with thick and deep longitudinal wrinkles, bark is easy to fall off to show white or light brown cortex, texture thereof is hard and brittle, broken off easily. The section is fibroid, yellow white, mealiness, has obvious rings and chrysanthemum core, has characteristic flavor, sweet in taste.<br>Ingredients:<br>0.72% of benzoic acid<br>volatile oil, fatty oil, resin<br>tannin<br>sugar, starch<br>lymphatic temperament<br>protein<br>paeoniflorin 1.8%~7.3% | Antitumor function:<br>Water or ethanol extractive of Radix Paeoniae Rubra can increase the content of cyclic adenosine monophosphate (cAMP) in tumor cells, so as to enhance anticancer action.<br>Antibacterial action:<br>It can inhibit *shigella dysenteriae*, *pseudomonas aeruginosa*, *staphylococcus aureus*, and damage the effect of aflatoxin B1. Benzoic acid can be used as preservative with other Chinese herbal medicine, has good curative effect on infectious acne.<br>Antithrombotic action<br>Paeoniflorin, d-catechin and analogous prostacyclin are powerful blood vessel relaxation agent, and inhibit platelet aggregation to have antithrombotic function.<br>Whitening effect:<br>Since having obvious effect on activating blood and dissolving stasis, it has effect on butterfly rash, freckle and pigment precipitate; it can be used for a long time because it is non-hormonal whitening expelling spot agent without any side effects.<br>Paeoniflorin also has sedation, analgesic, relieving spasm and anti-inflammatory effect.<br>Radix Paeoniae Rubra contains tannins which can affect the activity of SOD, therefore it has a powerful antioxidant ability. | Bitter in taste, slightly cold in nature, go into liver and spleen channel. Function includes clearing away heat and cooling blood, activating blood and dissolving stasis, detumescence analgesic. It is used for pyreticosis and eruption, traumatic injury, hot eyes etc.. In recent years, it can be used for treating arteria coronaria rencently. |
| Radix Linderae (Lauraceae) Alias: TongQianCai, TianTaiWuYao, Short ZhangGen Use part: dry root | Characters:<br>It is cylindrical or spindle, nodular enlargement, 5-15 cm in length, 0.5-2.5 cm in diameter, appearance is yellow brown to dark brown, have fine wrinkle ring crack and lateral root mark, the bark is easy to peel off and show fibrous wood, texture thereof is solid and is hard to break off. Section of part without bark is spherelike or irregular shape, cutting surface is light brown and reddish, radicals and annual rings are visible, aromatic in smell, slight flavour in taste, and has irritative cool.<br>Ingredients<br>linderalactone,<br>isolinderalactone,<br>isolinderoxide, linderene,<br>neolinderalactone,<br>isohexylfuran, laurolitsine,<br>sesquiterpenoids. | Gastrointestinal regulatory role<br>It has bidirectional effect on gastrointestinal smooth muscle, can promote or inhibit gastrointestinal activities.<br>Antibacterial aciton and treating herpes simplex virus Cultivating with virus can restrain virus with high efficiency.<br>Stop bleeding and promoting blood coagulation<br>Vitro experiments prove Radix Linderae powder can obviously reduce plasma calcification time, and promote blood coagulation.<br>Antihistamine action<br>Alcohol extractive of Radix Linderae root has antihistamine role on trachea of guinea pigs. | Spicy in taste, warm in nature. The function includes promoting qi circulation and relieving pain, warming kidney and eliminating cold. It is used for chest distress and costalgia, pain in gastral cavity, regurgitation and vomit, pain in belly caused by cold, line of abdominal pain, frequent urination and enuresis etc . . . |

TABLE 4-continued

| Medicinal materials | Characters and ingredients | Pharmacological action | Taste, nature and efficacy |
|---|---|---|---|
| Radix Angelicae Formosanae (Umbelliferae) Alias: Fragrant *angelica dahurica*, Aromatic chuan *angelica dahurica* Use part: root | Characters: Root is cone, surface is gray yellow to yellow brown. Hole in the bark is visible and scatters protuberantly in transverse, which is called "geda ding". Section is mealiness, and brown grease spots scatter in cortex, form ring, xylem accounts for about a third of the section, strongly fragrant in smell, taste sweet and slightly bitter. Ingredients: Containing volatile oil, many kinds of coumarin derivatives | Antimicrobial effect It has a certain inhibition effect on *escherichia coli*, *shigella dysenteriae*, *typhoid bacillus coli*, *paratyphoid bacillus*, *pseudomonas aeruginosa* and *proteus*, *choleraic vibrio* etc.. Antipyretic, analgesia and anti-inflammatory action Water extractive has a certain effect on detumescence for relieving pain and skin pruritus. Cosmetics It has the effect of whitening skin, sunscreen, prevent UV, but because containing furan coumarin compounds, it has photosensitivity Effect on fat metabolism It can enhance the fat decomposition function induced by adrenaline and ACTH, and inhibit glucose induced by insulin from changing into fat. | Spicy in taste, warm in nature. Function includes expelling wind and relieving exterior, relieving pain, treating nasal obstruction, detumescence and apocenosis, eliminating dampness and arrestin. It is used for headache by cold, superciliary ridge pain, gum pain, feeling fullness in the head, nasal obstruction, turbid nasal mucus, acute and chronic sinusitis, cold wet leucorrhea, clear leucorrhea, swelling and boils, acute mastitis pain, expelling wind and relieving itching, pruritus by wind etc . . . |
| Radix Angelicae Pubescentis (Umbelliferae) Alias: Fragrant angelicae Pubescentis, Large angelicae Pubescentis, Chuan angelicae Pubescentis, Yu Huo Use part: rhizome | Characters Taproot is slightly cylindrical, has branches, 10-30 cm in length. Reed head is enlargement, has many horizontal wrinkles, and has a diameter of 1.5-3 cm. There is stem and leaf residual bases or depression on the top, surface is greyish brown or brown, has longitudinal wrinkles, and has protuberance lenticel on bark in transverse and protuberant fine root marks. It is hard in texture, section has brown rings, bark is grey-white, brown grease spots scattered is visible; xylem is sallow to yellowish-brown. Ingredients: Coumarins such as Angelicon Angelol Bergapten Angelical Psoralen Byakangelicin | Treat arthritis, analgesic and sedation Rhizoma Notopterygii and Radix Angelicae Pubescentis can expel rheumatism, but efficacy of Rhizoma Notopterygii is larger and acute, it gets into taiyang (bladder) channel, is good at treating headache caused by rheumatism (one with more severe occipital pain, the efficacy is better), limbs pain and body pain. Powder of Radix Angelicae Pubescentis is milder than Rhizoma Notopterygii, it gets into shaoyin channel (kidney channel), is good at treating wind of shaoyin channel, mainly used for pain of waist, knees and foot shin. Directly dilating blood vessels and lower blood pressure Dogs and cats are given crude preparation of Radix Angelicae Pubescentis by intravenous injection, which has antihypertensive effect, but is not lasting, additionally, it has the effect of shrinking blood vessels. Effect on platelet aggregation It has influence on platelet aggregation of rats, and may reduce the formation of vein thrombosis. Photosensitive role Radix Angelicae Pubescentis contains furan coumarin compounds such as Bergapten, xanthotoxin, which are photosensitive, can lead to photo sensitivity when shined by sun or UV. Antibacterial action | Spicy and bitter in taste, slightly warm in nature. Function iludes expelling rheumatism, relieving pain, removing obstruction, eliminating cold and relieving exterior. It is used for wind-cold-dampness arthralgia, arthralgia, achiness in loin and knees, paralysis in two feet, stretch disadvantage and wind-cold exterior syndrome with damp evil etc., is also applied for diaphoresis, sedation, diuresis and shrinking blood vessels. |

TABLE 4-continued

| Medicinal materials | Characters and ingredients | Pharmacological action | Taste, nature and efficacy |
|---|---|---|---|
| | | Furan coumarin compounds in the status of light sensitivity generally have no obvious antibacterial activity, but can kill bacteria upon exposure. But rats are given xanthotoxin and bergapten by intravenous injection, LD50 are respectively 160 mg/kg, 945 mg/kg. | |
| Radix Angelicae Sinensis (Umbelliferae) Alias: Yun Gui, Gan Gui, Qing Gui, Xi Dang Gui Use part: root | Characters: Root head and Taproot are rough, there are bud mark, stem base and petiole base remained on the top. There are more than 10 tails under root head and taproot, tail is thick above and thin below, many of which is distortion. Surface has fibrous root mark like knots. It is dry, hard in texture, become soft and pliable in texture when absorbing moisture. Section is yellow white with cranny; there are light brown rings and many brown oil spots in the middle layer. Greatly fragrant in smell, sweet and slightly spicy in taste. Ingredients Volatile oil: Acidity: (2%; palmitic acid, phthalic anhydride) Phenolic: (10%; carvacrol) Neutral: (88%, two kinds of sesquiterpene, n-butylidene phthalide, angelica ketone) Water-solubility: ferulic acid, angelica polysaccharide, stigmasterol-D-glucoside etc. Cholate, 17 kinds of amino acid 23 kinds of inorganic elements | Have anti-thrombotic and antanemic effect, improve liver and lung Relieving thrombus formation, promoting the generation of hemoglobin and the red blood cells. For chronic liver disease, relieving the liver fibrosis and promoting liver cell function recover. Improving lung ventilation function, strengthening physical strength. Have immune and anticancer effect, antiinflammation and Antibacterial action Ferulic acid sodium and angelica polysaccharide can ascend phagocytosis of macrophages, promote lymphocyte transformation, can be used for the treatment of cancer, especially for gynecological tumors. The effect of angelica extractive on vascular permeability and inhibiting platelet causing inflammation is similar with aspirin. Inhibiting golden *staphylococcus*, *pseudomonas aeruginosa* and *colibacillus*. Anti-aging action Ferulic acid can inhibit lipid peroxidation, and directly eliminate radicals. | Sweet and spicy in taste, warm in nature. Function includes hematogenesis and activating blood circulation, relieving constipation with laxatives. It is used for blood deficiency and chlorosis, palpitations and dizziness, abnormal menstruation, amenorrhea and dysmenorrhea, deficiency-cold abdominal pain, intestinal dry constipation, rheumatic arthralgia, traumatic injury, carbuncle and ulcer. Used with alcohol can activate blood circulation and have emmenagogic effect. It is used for treating amenorrhea and dysmenorrhea. |
| Myrrha (Burseraceae) Alias: Mo Yao, Ming Mei Yao Use part: resin spilled from myrrha bark | Characters: It is irregular particles, or sticks into mass, with a diameter of about 2.5 cm, has smaller or larger ones. Surface is red brown or yellow brown, rough, is covered with powder. It is hard and brittle in texture, easy to craze, the section is in the form of particle, has brown luster, is translucent, often has white spots or texture, has characteristic flavor, very bitter in taste. Main ingredients: Resin is 25-35%, volatile oil is 2.5-9%, gum is about 57-65%, water and various kinds of tannins is about 3-4%. Myrrh terpenol includes eugenol, meta-cresol, cuminaldehyde, pinene, cinene, limonene, cinnamaldehyde, heerabolene, etc. Gum is hydrolyzed into arab sugar, galactose and xylose. | Antiatheroscloresis The part containing resin oil can reduce high cholesterol of male rabbit fed with hydrogenated oil, can prevent the formation of artery wall plague, also reduce rabbit weight. Convergent effect Myrrh tincture has the convergent effect on mucous membrane, it can be used as oral lotion when occurring oral cavity and pharynx ulcer, and it is also used for stimulating intestines and stomach peristalsis. Anti-inflammatory, analgesic and defervescence 500 mg/kg of Myrrh extractive is applied to rat by stomach irrigation; it has significant inhibition effect on inflammation, which is called defervescence reaction. Antibacterial action Water extractive of Myrrh has different degree of effect on various pathogenic fungi such as tinea bacteria in tube. | Bitter and spicy in taste, neutral in nature, nontoxic. Function includes activating blood circulation and removing blood-stasis, removing bruises and relieving pains, treating traumatic injury, pain in bones and heart, abdominal mass, gynecological mass, amenorrhea, ulcer and swelling, anal fistula, invisibility. The action of activating blood circulation and removing blood-stasis, removing bruises and relieving pains is similar with Olibanum. It is mainly applied for traumatic pain and amenorrhea etc., |

TABLE 4-continued

| Medicinal materials | Characters and ingredients | Pharmacological action | Taste, nature and efficacy |
|---|---|---|---|
| | | | also used for chest pain in heart and chest caused by qi stagnancy and blood stasis. |
| Rhizoma Notopterygii (Umbelliferae) Alias: Chuan Qiang, Kuan Ye Qiang Huo, Chan Qiang, Hei Yao Use part: dry root, rhizome | Charaters: Rhizome is cylindrical, has different length, with a diameter of 1-3 cm. Appearance is brown-black, node is dense in the upper section, and rare in the lower section, has ridgy rings, has many bud mark like strumae, has stem mark on the top. Root is cylinder or cone with microgroove and branch root mark. It is loose in texture, section is not smooth, yellow white, delicate fragrance, slightly spicy and bitter later in taste. Cross section or oblique section slice is round or oblate, there is chrysanthemum texture on the surface, the bark is brownish red, xylem is white, medulla is brown to black in the center, loose into hollow. Ingredients: Main ingredients: including volatile oil which is identified to be 20 types, accounting for 97.13%. Non-volatile oil contains columbianadin, notopterol, ferulic acid and coumarin. | Antipyretic, analgesic and anti-inflammatory effect Rats test shows that it has antipyretic ability, clippling tail and burning tail test shows that Rhizoma Notopterygii has obvious analgesic effect, additionally, anti-swelling experiment shows that Rhizoma Notopterygii has antiphlogistic effect. Effect against myocardial ischemia Volatile oil of Rhizoma Notopterygii can dilate coronary artery, increase coronary artery flow, and improve the state of the myocardial ischemia. Antibacterial action In culture dish test, Rhizoma Notopterygii oil has obviously inhibiting effect on *dysentery bacillus*, *escherichia coli*, *pseudomonas aeruginosa*, and golden *staphylococcus aureus*. | Bitter and spicy in taste, warm in nature. Function includes expelling wind and relieving exterior, relieving pain and spasmolysis. It is used for cold, fever by cold, rheumatic arthralgia, headache, body pain, tetanus etc. It has antibacterial action, diaphoresis, antipyretic action and analgesia. |
| Cortex Cinnamomi (Lauraceae) Alias: Da Gui, Mu Gui, Yu Gui, La Gui, Jun Gui and Tong Gui Use part: bark | Characters It is in the form of shallow groove or cannular, with a length of 30-50 cm, a width or diameter of 3-10 cm, and a thickness of 2-8 mm. Surface is grey brown, a light coarse, with horizontally protruding skin holes and fine wrinkles. Inner is brownish red and smooth, has fine lines. It is hard and brittle in texture, section is graininess, outer layer is brown, inner layer is red brown and oily, there is a light yellow line (stone cells band) between two layers. The bark which is closer to the center of the trunk, has higher quality. Strong fragrant in smell, taste sweet and spicy. Ingredients: Volatile oil: cinnamaldehyde, cinnamyl acetate | Dilated effect on peripheral vessel Increasing myocardial contractility and times of heart beat, and dilating arteria coronaria, increasing blood flow Anticoagulation Cortex Cinnamomi extractive with methanol can inhibit platelet aggregation, cinnamic acid has antithrombin action. strengthening the stomach action and removing spasmodic pain of stomach Cortex Cinnamomi oil is aromatic stomachic carminative, can relieve the irritation on stomach and intestine, can enhance secretion of saliva and gastric juice, and remove smooth muscle spasm of stomach and intestine. Antiinflammation Cortex Cinnamomi has a certain inhibiting effect on acute and chronic inflammation, can inhibit feet swelling of rats and increase of capillary permeability. Antibacterial action Cinnamaldehyde has strong bactericidal action, especially for dermatophytes. | Bitter and sweet in taste, hot in nature. Function includes warm middle and relieve cold, warm kidney and promote yang, get through the meridians, warm qi and blood. It is used for pain by spleen and stomach deficiency and cold, chill and limbs cold, impotence and frequent micturition, yang deficiency of spleen and kidney, pain in belly and loose stool, amenorrhea by cold, pain in belly by amenorrhea, pain by cold and dampness, aeipathia weakness, weak qi and blood deficiency, swelling from yin carbuncle, there is no ulcer even if purulence forms, ulcer which is not healed for a long time, bladder deficiency and cold, urinary obstruction etc . . . |

TABLE 4-continued

| Medicinal materials | Characters and ingredients | Pharmacological action | Taste, nature and efficacy |
|---|---|---|---|
| Rhizoma Bletillae (Orchidaceae) Alias: Bai Ji, Lian Ji Cao, Bai Ji, Gan Gen, Zi Lan Gen Use part: rhizome | Characters It is flat like palm, young rhizome is fleshy, and branches are short. Surface is smooth and almost white, with a diameter of 2-3 cm and a thickness of about 3 mm, has stem scars, root tuber mark below, fine roots mark with brown tache, scale leaves like membrane. It is hard in texture, and is not easy to break off. Decoction pieces and transverse section slice are translucent and keroid, have scattered vascular bundle points. It has no flavor, light taste, is viscous. Ingredients: Tuber contains bibenzyl compounds, biphenanthrene compounds, biphenanthrene ethers compounds, dihydro-phenanthrene pyranoid compounds, phenanthrene derivative of spironolactone, glucoside compound of phenanthrene, benzyl compounds, anthracene compounds, acid substances and aldehyde. | Hemostasis Film prepared with extractive solution of Rhizoma Bletillae root tuber can be used for experimental wound bleeding of dogs and rabbits Protection for mucous membrane Reducing the damage of mucous membrane reduced by hydrochloric acid, but has no effect on gastric secretion. Anti-tumor effects Rhizoma Bletillae and Glucose Injection have obviously inhibiting effect on liver cancer of rats. | Bitter and sweet in taste, cold in nature. Function includes relieving cough, removing heat and detoxicating, promoting tissue regeneration, astringing wound. It is used for phthisis, cough, hemoptysis and traumatic injury. |
| Radix Et Rhizoma Rhei (Polygonaceae) Alias: Huang Liang, Jiang Jun, Huo Shen, Fu Ru Use part: rhizome | Characters One, north Radix Et Rhizoma Rhei is conical or toroidal shape, with a length of 5-17 cm and a diameter of 3-10 cm, bark therof has been removed or retains a little. Outer bark is yellowish-brown or reddish brown, has almost white rhombus mesh texture, which is commonly called as "Jin Wen", or has spiral "star" like chrysanthemum, one end often has rope hole. It is hard in texture, cross section is yellowish-brown, and has particles, slightly oily. In nearly peripheral place, it accidentally has dark cambium and radial orange bending lines, special smell, taste bitter and puckery slightly. Two, South Radix Et Rhizoma Rhei is loose in texture, very fibrous, has weak smell, the other is similar with north Radix Et Rhizoma Rhei. Ingredients; Main ingredients are anthraquinones derivative and tannin. | Effect on digestive system 1. Protecting liver and gallbladder. 2 Treating gastric and duodenum ulcer. 3 Cathasis. 4 Has effect on smooth muscle of bowel Effect on pathogene, microorganism and virus Have effect on bacteria, fungus and virus Effect on antitumor Mice are given rhein and emodin by intraperitoneal injection, have good inhibiting effect on melanin tumour and ehrlich ascites tumor of mice Antiinflammation Radix Et Rhizoma Rhei has obvious inhibiting effect on various animal trial inflammation, can be used for traumatic injury, pain from stasis. The powder can be placed on the wound besides internal use, which can improve blood circulation and relieve bruises and relieving pain Hemostasis Radix Et Rhizoma Rhei is used for hemostasis for a long time, | Bitter in taste, cold in nature. Function includes eliminating dampness and heat, discharging fire, cooling blood, eliminating stasis and detoxicating. It is mainly used for material constipation, mass in the abdomen by hot, diarrhea dysentery resulted from dampness and heat, jaundice, clap, edema and full abdomen, difficult urination, hot eyes, sore throat, tongue festered, stomach heat with vomiting, traumatic injury, pyretic toxicity, carbuncle and ulcer. |

| Medicinal materials | Characters and ingredients | Pharmacological action | Taste, nature and efficacy |
|---|---|---|---|
| | The content of anthraquinones derivative accounts for about 1-5%, free anthraquinones derivative contains rhein, archen, chrysophanol, aloe-emodin and physcion. Combined anthraquinones derivative contains double anthraquinone glycosides and single anthraquinone glycoside. The content of tannin accounts for about 5%, contains galloyl glycosides, catechin, gallic acid and tetrarin. | especially, efficacy in treating digestive tract bleeding has been confirmed in recent years | |

The Chinese herbal medicine extractive of the present invention can be prepared by the process according to the first embodiment of the present invention. As shown in FIG. 1, process according to the first embodiment of the present application comprises the following steps: in Step 100, providing the first type of medicinal materials and the second type of medicinal materials, wherein, the first type of medicinal materials include Rhizoma Bletillae, Cortex Cinnamomi, Radix Angelicae Formosanae, Radix Angelicae Sinensis, Paeonia Lactiflora (such as Radix Paeoniae Rubra, Radix Paeoniae Alba), Rhizoma Notopterygii, Radix Linderae, Glycyrrhizae, Radix Angelicae Pubescentis, and Radix Et Rhizoma Rhei, which are basic medicinal materials. The second type of medicinal materials is one, two or three selected from the group consisting of *Zingiber Officinale* (such as Rhizoma Zingiberis, *Zingiber Officinale Roscoe*), *Olibanum* and *Myrrha*, which are added medicinal materials. In Step 102, adding organic solvent (such as one or more selected from methanol, ethanol, acetone, methyl ethyl ketone, kerosene (petroleum ether) and hexane), putting the first and second type of medicinal materials and the organic solvent in the first container (that is extraction bucket), make the percent by weight between the first and second type of medicinal materials and the organic solvent reach 1:N, so as to form the mixed solution, N is a number between 3 and 12. Preferably, N is 8. In Step 104, heating the mixed solution to a predetermined temperature and performing the extraction for a predetermined time, so as to carry out the extraction, wherein the predetermined temperature is between 30° C. and 100° C. If the organic solvent is ethanol, the predetermined temperature is preferably within the range of boiling point of ethanol±5° C. The predetermined time is between 1 h and 6 h. In Step 106, filtering the mixed solution while hot, achieving the filtrate and transferring it to the second container (that is measuring glass). In Step 108, condensing the filtrate into an extractum with a water content in the range of 10-40% by weight and a content of the organic solvent in the range of 3-30% by weight. Preferably, condensing the filtrate into an extractum with a water content in the range of 10-20% by weight and a content of organic solvent in the range of 5-10% by weight. The extractum is an intermediate product, which is convenient to be transported and saled, so as to prepare the final product. In Step 110, removing the residue from the container.

Figure 2:
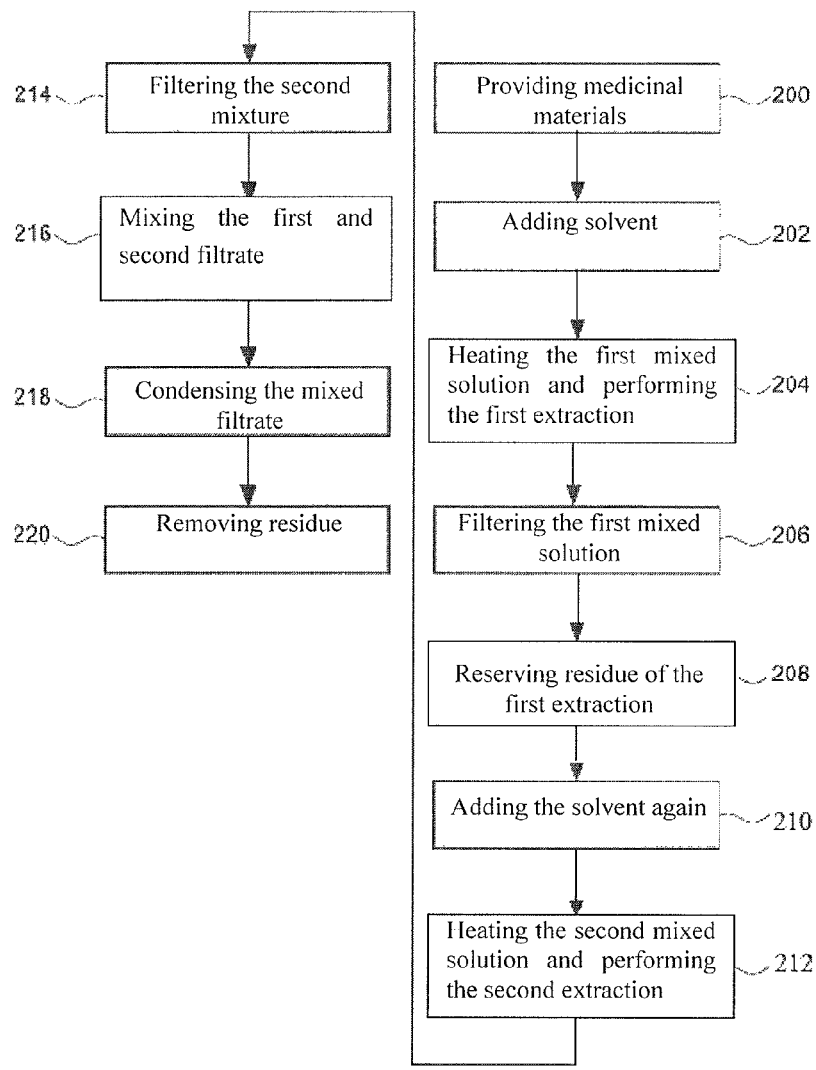
FIG. 2 is a flow chart for illustrating the second embodiment of the preparation method according to the present invention.

The Chinese herbal medicine extractive of the present invention can be prepared by the process according to the second embodiment of the present application. As shown in FIG. 2, the process according to the second embodiment comprises the following steps: in Step 200, providing the first type of medicinal materials and the second type of medicinal materials, wherein, the first type of medicinal materials include Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei, which are basic medicinal materials. The second type of medicinal materials is one, two or three selected from the group consisting of *Zingiber Officinale, Olibanum* and *Myrrha*, which are added medicinal materials. In Step 202, adding organic solvent, putting the first and second type of medicinal materials in the first container with organic solvent (that is extraction bucket), make the percent by weight of the first and second type of medicinal materials with the organic solvent reach 1:N, so as to form the mixed solution, N is a number between 3 and 12. Preferably, N is 8. In Step 204, heating the mixed solution to a first predetermined temperature and performing the extraction for a first predetermined time, so as to carry out a first extraction, wherein the first predetermined temperature is between 30° C. and 100° C. If the organic solvent is ethanol, the first predetermined temperature is preferably within the range of boiling point of ethanol±5° C. The first predetermined time is between 1 h and 6 h. In Step 206, filtering the first mixed solution while hot, achieving the filtrate and transferring it to the second container (that is measuring glass). In Step 208, reserving the residue from the first extraction. In Step 210, adding the organic solvent again, making the percent by weight of the above medicinal materials with the organic solvent reach 1:N again, so as to form a second mixed solution, N is a number between 3 and 12. Preferably, N is 8. In Step 212, heating the second mixed solution to a second predetermined temperature and performing the extraction for a second predetermined time, so as to carry out the second extraction, wherein the second predetermined temperature is between 30° C. and 100° C. If the organic solvent is ethanol, the second predetermined temperature is within the range of boiling point of ethanol±5° C. The second predetermined time is between 1 h and 6 h. In Step 214, filtering the second mixed solution while hot, achieving the filtrate of the second extraction. In Step 216, mixing the filtrate of the first extraction and the filtrate of the second extraction. In Step 218, condensing the mixed filtrate into an extractum with a water content in the range of 10-40% by weight and a content of organic solvent in the range of 3-30% by weight. Preferably, condensing the mixed filtrate into an extractum with a water content in the range of 10-20% by weight and a content of organic solvent in the range of 5-10% by weight. The extractum is an intermediate product, which is convenient to be transported and saled, so as to prepare the final product. In Step 220, remove the residue of the second extraction from the container.

Figure 3:
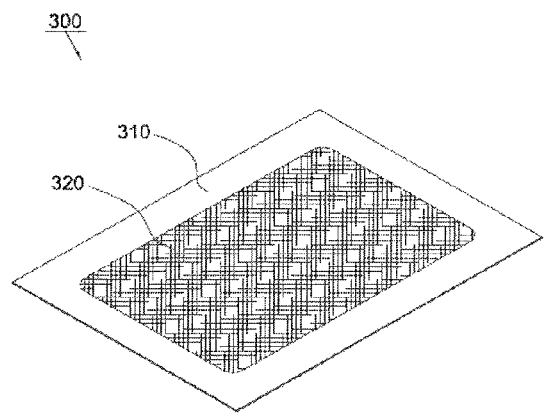
FIG. 3 is a stereoscopic diagram for showing the Chinese herbal medicine patch having the Chinese herbal medicine composition according to the present invention.

As shown in FIG. 3, the Chinese herbal medicine extractive of the present invention can be used in Chinese herbal medicine patch 300. Wherein the Chinese herbal medicine patch 300 comprises adhesive tape layer 310 and Chinese herbal medicine layer 320. The Chinese herbal medicine layer 320 is formed on the adhesive tape layer 310. In the embodiment, the Chinese herbal medicine layer comprises diluent and extractum of the Chinese herbal medicine according to the present invention. The extractum of the Chinese herbal medicine (intermediate product) is mixed with the diluent, so as to form the Chinese herbal medicine layer (final product). The diluent includes ethanol, water and water-based glue. The Chinese herbal medicine patch 300 has a content of the Chinese herbal medicine extractive in the range of 50-3500 mg/14 g (each piece of the Chinese herbal medicine patch).

Figure 4:
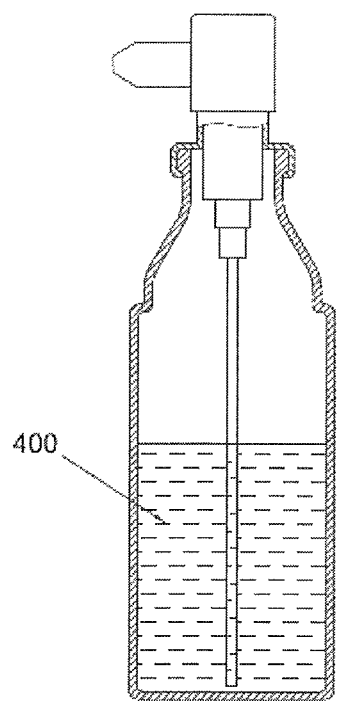
FIG. 4 is a section drawing for showing the Chinese herbal medicine spray having the Chinese herbal medicine composition according to the present invention.

As shown in FIG. 4, the Chinese herbal medicine extractive of the present invention can be used in Chinese herbal medicine spray. In the embodiment, the Chinese herbal medicine spray 400 comprises diluent and the extractum of the Chinese herbal medicine according to the invention. The extractum of the Chinese herbal medicine (intermediate product) is mixed with the diluent, so as to form the Chinese herbal medicine spray (final product). The diluent includes ethanol, polyalcohol and water. The Chinese herbal medicine spray has a content of the Chinese herbal medicine extractive in the range of 10-500 mg/g. In another embodiment, the Chinese herbal medicine spray does not contain the extractum obtained by condensed (intermediate product), but contains the filtrate obtained by the extractive without condensing (that is also an intermediate product), such that reducing the condensing procedures, leading to the shorten preparation time and reduced preparation cost.

Figure 5:
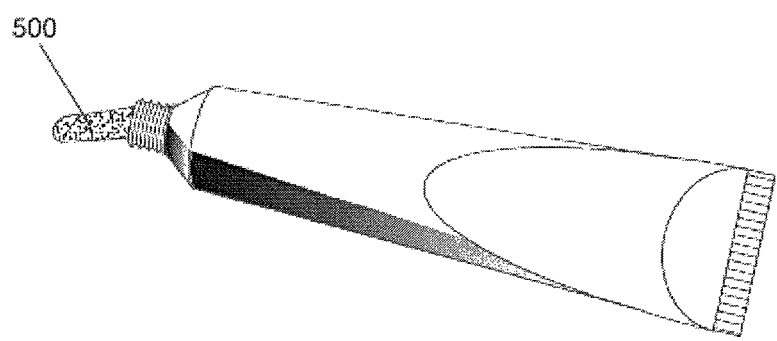
FIG. 5 is a stereoscopic diagram for showing the Chinese herbal medicine paste having the Chinese herbal medicine composition according to the present invention.

As shown in FIG. 5, in the embodiment of the invention, the Chinese herbal medicine extractive can be used in Chinese herbal medicine paste 500, which can be divided into ointment, hydrogel and cream. The Chinese herbal medicine paste 500 comprises diluent and the extractum of the Chinese herbal medicine extractive according to the present application. The extractum of the Chinese herbal medicine extractive (intermediate product) is mixed with the diluent, so as to form the Chinese herbal medicine paste (final product). As for the ointment, the diluent comprises vaseline, white wax and nonionic surfactant; as for the hydrogel, the diluent comprises ethanol, water and nonionic surfactant; as for the cream, the diluent comprises grease, wax and emulsifier. The Chinese herbal medicine paste 500 has an average content of the Chinese herbal medicine extractive in the range of 10-500 mg/g.

Furthermore, the Chinese herbal medicine extractive of the present invention can be used for oral preparation, which can be divided into powder, pills and lozenge. In the embodiment, the oral preparation comprises diluent and the extractum of the Chinese herbal medicine extractive of the present application. The extractum of the Chinese herbal medicine extractive (intermediate product) is mixed with the diluent, so as to form the oral preparation (final product). As for the powder and pills, the diluent comprises starch and saccharides (such as sugar or honey); as for the lozenge, the diluent mainly comprises crystalline cellulose. The oral preparation has a content of the Chinese herbal medicine extractive in the range of 3-250 mg/g.

Additionally, the above-mentioned Chinese herbal medicine extractive comprises the following 9 types of main indicative ingredients: Paeoniflorin, Ferulic acid, Cinnamaldehyde, Glycyrrhizin, Rhein, Imperatorin, Osthol, Isoimperatorin and Gingerol. Based on 1 g of the Chinese herbal medicine extractive, the content of the indicative ingredients is respectively that, Paeoniflorin is 4.466-1.488 mg, Ferulic acid is 0.382-0.127 mg, Cinnamaldehyde is 2.159-0.720 mg, Glycyrrhizin is 9.677-3.226 mg, Rhein is 1.013-0.338 mg, Imperatorin is 0.727-0.242 mg, Osthol is 1.389-0.463 mg, Isoimperatorin is 0.709-0.236 mg, Gingerol is 0.144-0.432 mg.

The invention is further illustrated by the following test examples and test data.

Test Example 1

The irritant of each extractum of the Chinese herbal medicine on animal skin is tested.

The each medicinal material in original formula of Panchrest plaster and the formula of the Chinese herbal medicine composition in the present invention is respectively put in an extractor with 95 wt % ethanol at a ratio of 1:8 by weight, and is extracted for 3 h at 80° C., the extractive is repeated twice, two parts of extracting solution are collected, then filtrated separeately, the filtrate is condensed by a reduced pressure concentrator. 25 μL of the extractum, positive control and negative control substance is respectively applied to the skin of an animal eliminated the hair on the back. After irritation for 24 h, the skin reaction is observed and recorded after 24 h, 48 h and 72 h. According to the dermal irritation scoring system evaluation method (as shown in Table 5) and Primary Dermal Irritation Index (as shown in Table 6), the degree of dermal irritation is evaluated (as shown in Table 7).

TABLE 5

Dermal irritation scoring system evaluation method

| Dermal response | Score |
| --- | --- |
| Erythema and Eschar Formation | |
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |
| Necrosis (depth of tissue) | +N |
| Eschar (sloughing or scab formation) | +E |
| Edema Formation | |
| No edema | 0 |
| Very slight edema (barely perceptible) | 1 |
| Slight edema (edges of area well-defined by definite raising) | 2 |
| Moderate edema (raised approximately one millimeter) | 3 |
| Severe edema (raised more than one millimeter and extending beyond the area of exposure) | 4 |

TABLE 6

Primary Dermal Irritation Index

| PDII = 0 | Nonirritant |
| --- | --- |
| PDII = 0.0-0.5 | Negligible irritant |
| PDII = 0.5-2.0 | Mild irritant |
| PDII = 2.0-5.0 | Moderate irritant |
| PDII = 5.0-8.0 | Severe irritant |

Primary Dermal Irritation Index (PDII) = score/observed times
Observed times = Observed days × number of tested animals
Results: the higher PDII score is, the stronger dermal irritant is

TABLE 7

Degree of dermal irritation

| | Ingredient | PDII |
|---|---|---|
| 1 | PC | 1.33 |
| 2 | Radix Angelicae Formosanae | 0.33 |
| 3 | Rhizoma Notopterygii | 1.00 |
| 4 | Radix Sophorae Flavescentis | 0.00 |
| 5 | Rhizoma Bletillae | 0.56 |
| 6 | *Momordica Cochinchinensis* | 4.00 |
| 7 | Radix Scrophulariae | 0.56 |
| 8 | Radix Rehmanniae | 0.56 |
| 9 | *Ampelopsis Japonica* | 0.22 |
| 10 | *Glycyrrhiza* | 0.22 |
| 11 | Radix Linderae | 0.33 |
| 12 | Radix Paeoniae Rubra | 0.33 |
| 13 | Cortex Cinnamon | 0.78 |
| 14 | Radix Aconiti Kusnezoffii | 0.89 |
| 15 | Radix Aconiti | 1.00 |
| 16 | Radix Angelicae Sinensis | 0.78 |
| 17 | Radix Angelicae Pubescentis | 0.44 |
| 18 | Radix Et Rhizoma Rhei | 0.33 |
| 19 | Rhizoma Zingiberis | 1.80 |
| 20 | Olibanum | 0.00 |
| 21 | Myrrha | 0.00 |
| 22 | Panchrest plaster | 2.78 |
| 23 | Extractum of the present invention | 0.00 |
| 24 | NC | 0.00 |

Note:
PC (positive control) is 1 wt. % 2,4-Dinitrochlorobenzen
NC (negative control) is $H_2O$.

As shown in Table 7, although a part of medicinal materials in the Chinese herbal medicine composition of the present invention have mild irritation, the extractum of the present invention is nonirritant. However, panchrest plaster has moderate irritant.

tent of indicative ingredients (Paeonia Lactiflora, Radix Angelicae Sinensis, Cortex Cinnamomi, Glycyrrhizae, Radix Et Rhizoma Rhei, Radix Angelicae Formosanae, Radix Angelicae Pubescentis, Rhizoma Notopterygii) is calculated respectively, by comparing the extraction results of medicinal materials under different conditions, the optimal medicinal materials extraction condition is optimized. The result is shown in Table 8.

TABLE 8

Different extraction condition for 13 kinds of medicinal materials in the Chinese herbal medicine composition formula in the present invention

| No. | Filtrating solition | Temperature | Ratio between medicinal materials and filtrating solution | Extracting time |
|---|---|---|---|---|
| PN-1 | 95 wt % ethanol | 80° C. (boiling) | 1:8 | Three hours for twice |
| PN-2 | 75 wt % ethanol | 80° C. (boiling) | 1:8 | Three hours for twice |
| PN-3 | 50 wt % ethanol | 80° C. (boiling) | 1:8 | Three hours for twice |
| PN-4 | 25 wt % ethanol | 80° C. (boiling) | 1:8 | Three hours for twice |
| PN-5 | 0 wt % ethanol | 80° C. (boiling) | 1:8 | Three hours for twice |
| PN-7 | 95 wt % ethanol | 50° C. | 1:8 | Three hours for twice |
| PN-8 | 95 wt % ethanol | 0° C. | 1:8 | Three hours for twice |

The average content of the indicative ingredients by milligram in 1 g of the extracting solution of medicinal materials by HPLC under different conditions (n=3), the result is shown in Table 9. As can be seen from Table 9, the 95 wt % to 50 wt % of ethanol or higher temperature is used; more indicative ingredients can be achieved by extracting.

TABLE 9

| No. | Paeoniflorin | Ferulic acid | Cinnamaldehyde | Glycyrrhizin | Rhein | Imperatorin or isopsoralen | Osthol or osthole | Isoimperatorin | Gingerol |
|---|---|---|---|---|---|---|---|---|---|
| PN-1 | 2.97792 | 0.25490 | 1.43932 | 6.45148 | 0.67543 | 0.48444 | 0.92621 | 0.47271 | 0.28772 |
| PN-2 | 2.29726 | 0.20914 | 1.07004 | 4.06984 | 0.48820 | 0.36641 | 0.66010 | 0.37264 | 0.27733 |
| PN-3 | 2.26606 | 0.23524 | 0.47223 | 4.63019 | 0.43297 | 0.29041 | 0.64084 | 0.28347 | 0.27321 |
| PN-4 | 1.89943 | 0.18855 | 0.08628 | 3.79355 | 0.35678 | 0.07382 | 0.19051 | 0.06720 | 0.24432 |
| PN-5 | 2.04702 | 0.16077 | 0.00000 | 1.97975 | 0.19599 | 0.00000 | 0.02403 | 0.01587 | 0.13765 |
| PN-7 | 1.95302 | 0.09867 | 1.32801 | 2.35790 | 0.39206 | 0.39484 | 0.58352 | 0.36948 | 0.23519 |
| PN-8 | 1.63157 | 0.07588 | 1.29591 | 1.17364 | 0.21043 | 0.32561 | 0.70000 | 0.32067 | 0.17769 |

Test Example 2

Preferable Extraction Condition for the Medicinal Materials in the Chinese Herbal Medicine Composition Formula of the Present Invention Thirteen kinds of medicinal materials in the Chinese herbal medicine composition formula in the present invention are mixed at equal proportion or various proportion, and extracted and condensed at different conditions (temperature, organic solvent), then detected by high performance liquid chromatography (HPLC) after proper dilution, and the con- Test Example 3

HPLC Chromatograms for Each Kind of Medicinal Materials in the Chinese Herbal Medicine Composition Formula in the Present Invention 1 g of each kind of medicinal materials is respectively put into an extractor with 8 g of 95 wt % ethanol, and extracted for 3 h at 80° C., the extraction is repeated twice, and two parts of extracting solution are collected, then filtered separately, the obtained filtrate is condensed into extractum by a reduced pressure concentrator, and then quantified to 150.0 mL by adding methanol (MeOH) as test solution. The high performance liquid chromatography analysis is performed by injecting 10 μL of the test solution, and then the fingerprints as shown in FIGS. 6A to 6L are established.

Figure 6A:
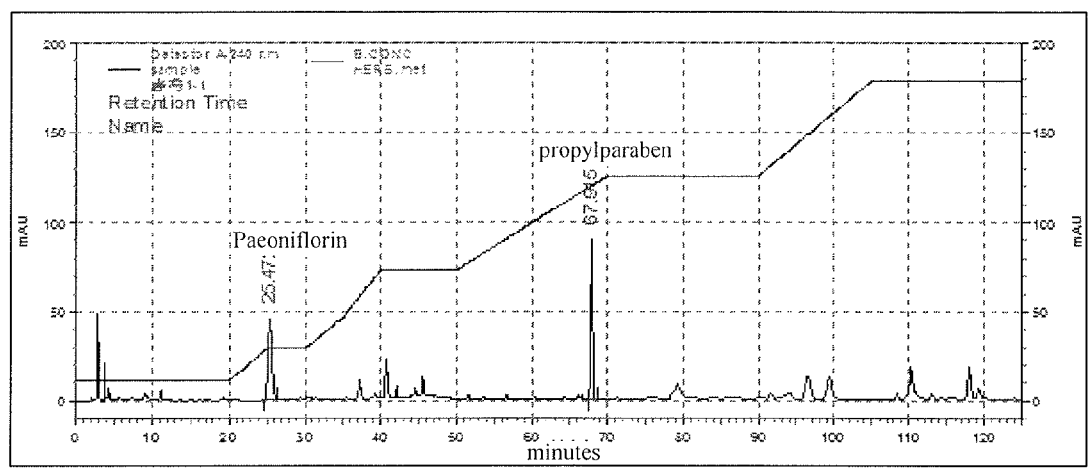
FIGS. 6A to 6L are fingerprints for each kind of medicinal material analyzed by HPLC.
Figure 6B:
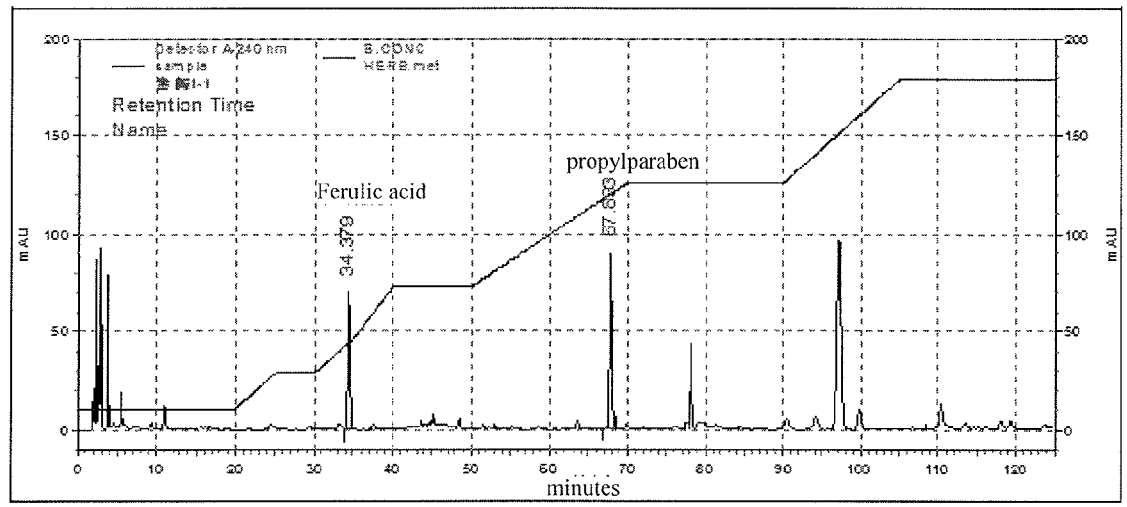
Figure 6C:
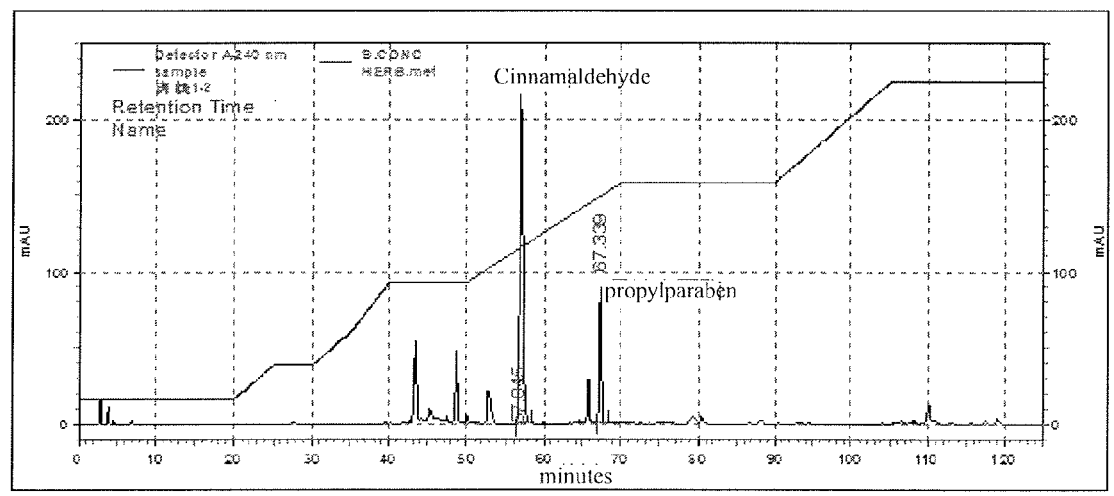
Figure 6D:
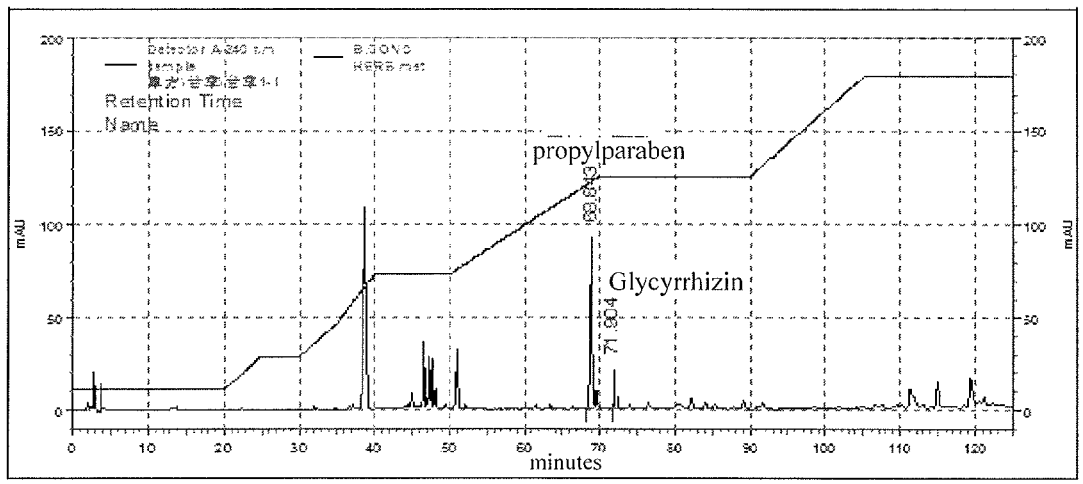
Figure 6E:
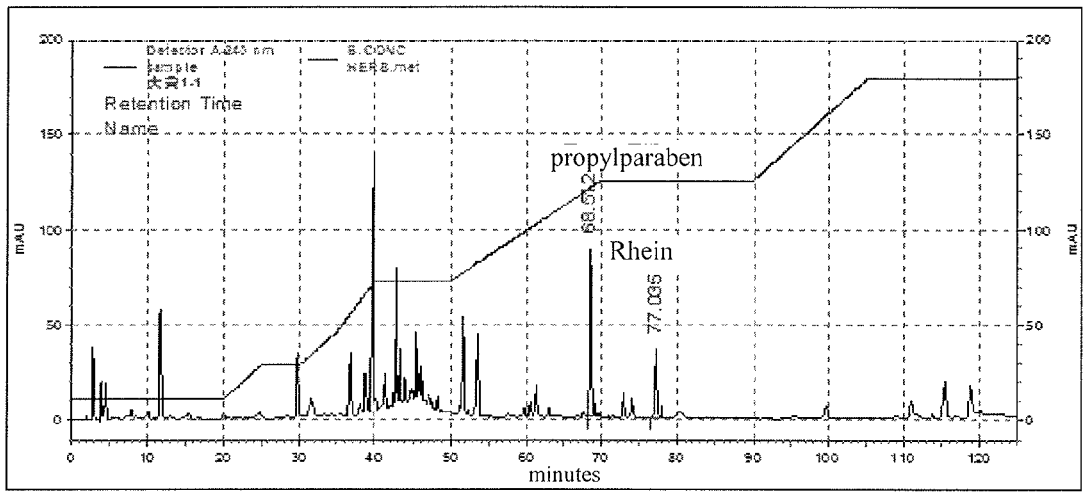
Figure 6F:
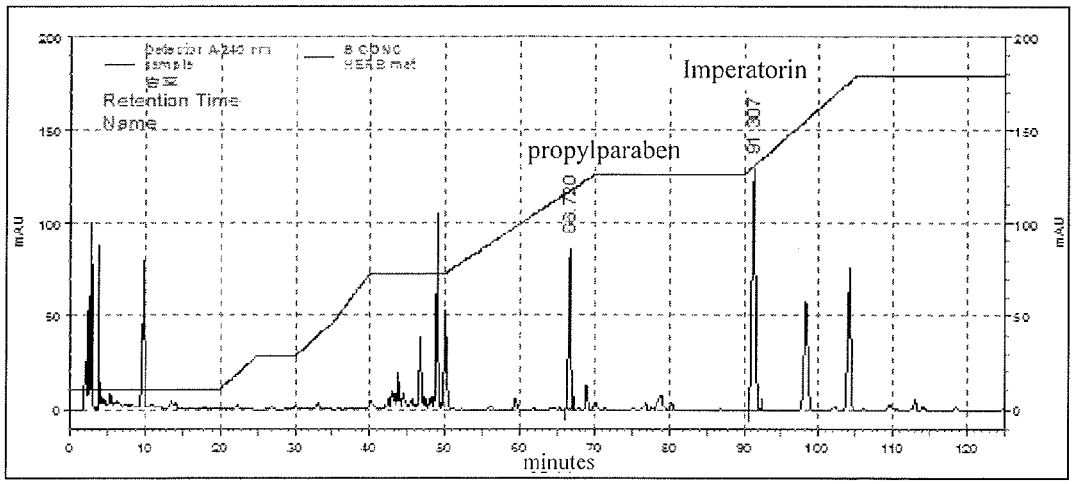
Figure 6G:
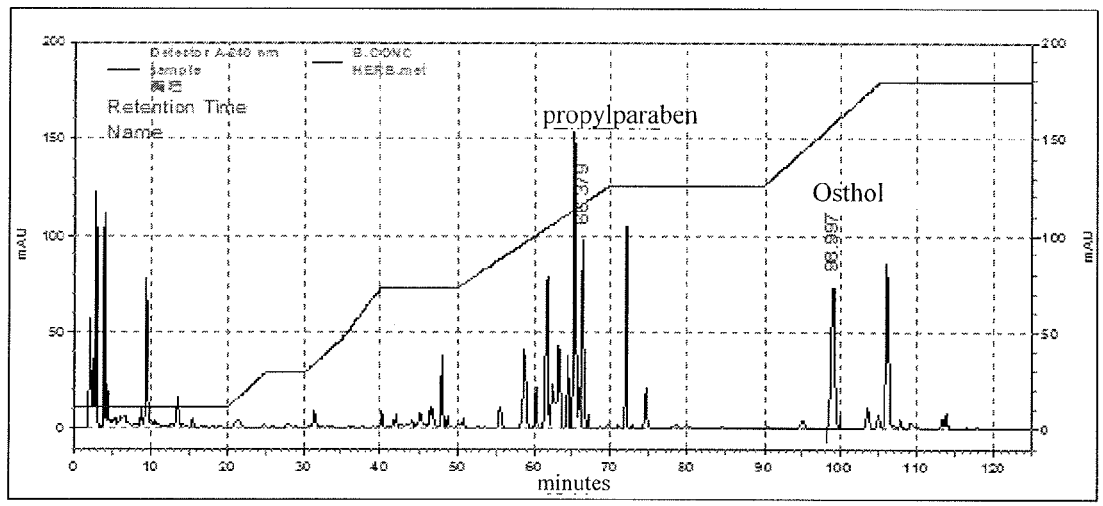
Figure 6:
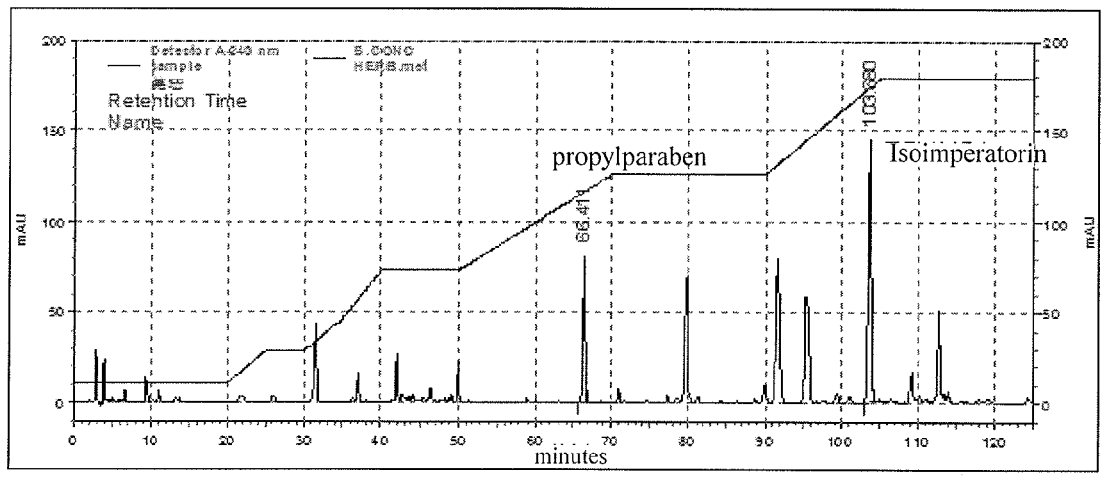
Figure 6I:
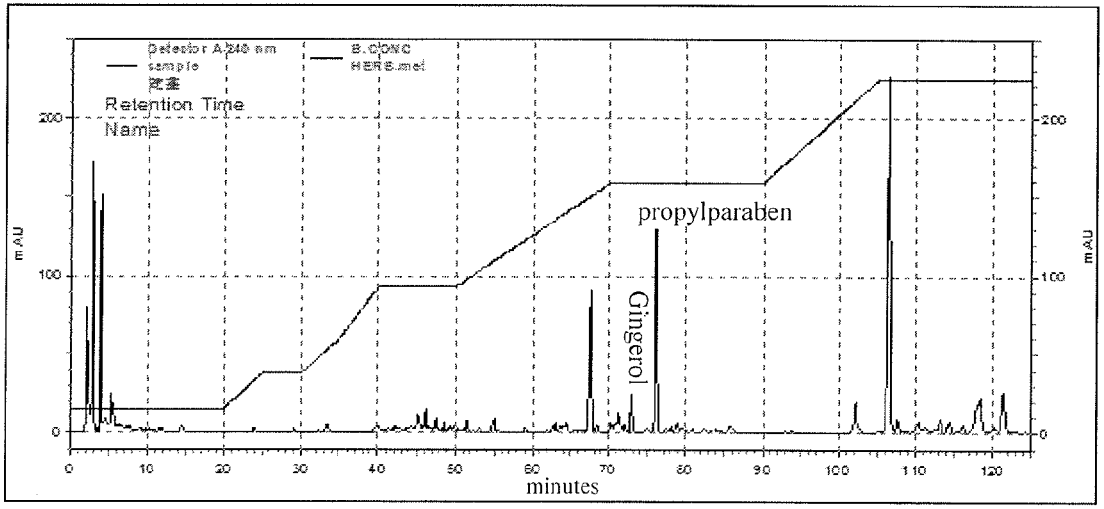
Figure 6J:
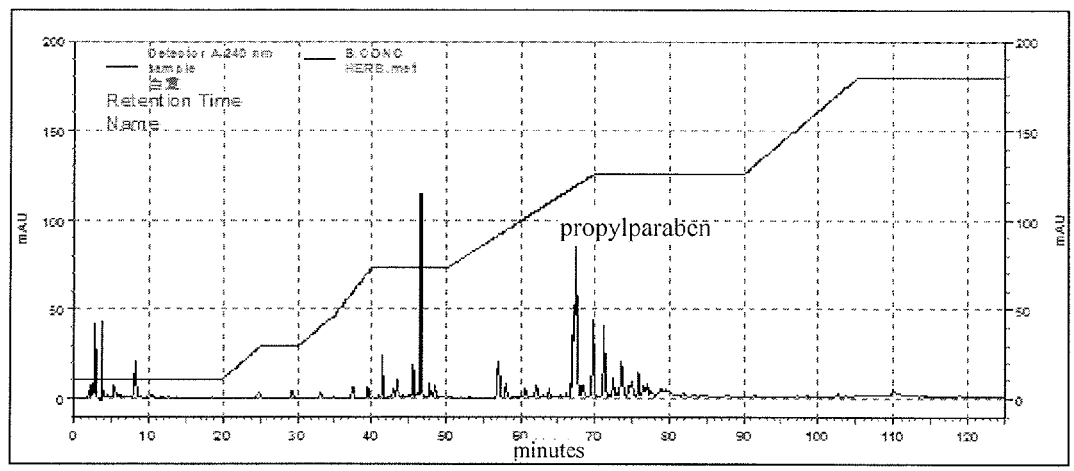
Figure 6K:
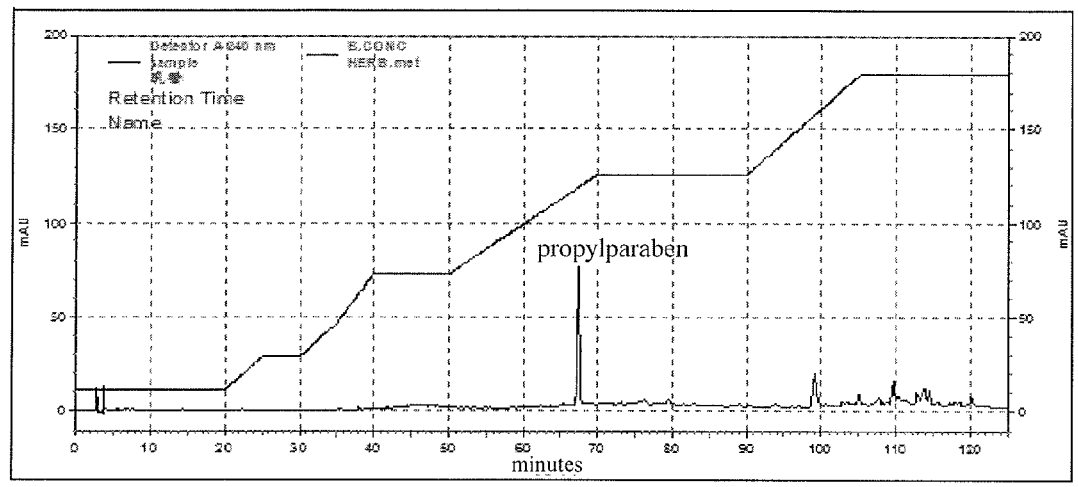
Figure 6L:
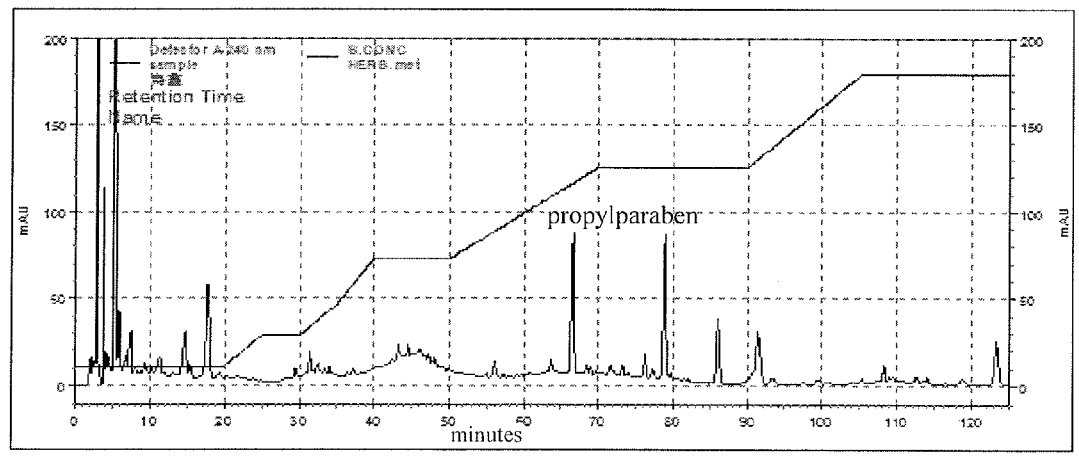

Wherein, FIG. 6A is the HPLC fingerprint of Radix Paeoniae Rubra and the indicative ingredient is Paeoniflorin;

FIG. 6B is the HPLC fingerprint of Radix Paeoniae Sinensis and the indicative ingredient is Ferulic acid;

FIG. 6C is the HPLC fingerprint of Cortex Cinnamon and the indicative ingredient is Cinnamaldehyde;

FIG. 6D is the HPLC fingerprint of Glycyrrhiza and the indicative ingredient is Glycyrrhizin;

FIG. 6E is the HPLC fingerprint of Radix Et Rhizoma Rhei and the indicative ingredient is Rhein;

FIG. 6F is the HPLC fingerprint of Radix Angelicae Formosanae and the indicative ingredient is Imperatorin or Isopsoralen;

FIG. 6G is the HPLC fingerprint of Radix Angelicae Pubescentis and the indicative ingredient is Osthol or Osthole;

FIG. 6H is the HPLC fingerprint of Rhizoma Notopterygii and the indicative ingredient is Isoimperatorin;

FIG. 6I is the HPLC fingerprint of Rhizoma Zingiberis;

FIG. 6J is the HPLC fingerprint of Rhizoma Bletillae;

FIG. 6K is the HPLC fingerprint of *Olibanum*;

FIG. 6L is the HPLC fingerprint of Radix Linderae.

Test Example 4

HPLC Chromatograms for the Chinese Herbal Medicine Composition Formula in the Present Invention 1 g of each kind of medicinal materials in the Chinese herbal medicine composition formula of the present invention is mixed each other and to obtain 13 g mixture, the mixture is added into an extractor with 104 g of 95wt % ethanol, then extracted for 3 h at 80° C., and filtered and the filtrate is achieved, the resulted residue is treated by the above-mentioned procedure again, two parts of extracting solution are collected and filtered, and the filtrate is condensed into an extractum by a reduced pressure concentrator, and then quantified into 150.0 mL by adding methanol (MeOH) as test solution. The high performance liquid chromatography analysis is performed by injecting 10 μL of the test solution, and then the fingerprints as shown in FIG. 7 are established.

Test Example 5

Percutaneous Experiment of the Medicine Materials Ingredient According to the Present Invention Test animals are Wistar rats (weight was about 250 g). During the test, test animals can eat and drink water freely. Test sample is the extractum from the Chinese herbal medicine. Rats are killed by breaking the cervical vertebrae, and are shaved off the belly hair with electric shaver, then the belly skin is removed. The removed skin, inner of which is moisted by normal saline, is clamped between the Donor cell and Receptor cell of Transdermal Franz Cell System. The test sample is dissolved in proper solvent, then placed in the Donor cell. Receptor cell is full of normal saline (containing 20 wt % of polyethylene glycol 400). The percutaneous experiment is carried at a constant temperature of 37° C. and at a fixed stiring speed of 500 rpm, and is sampled at a time of 3 h, 6 h, 12 h, 24 h, 36 h and 72 h. The sample is injected into the high performance liquid chromatograph spectrometer to analyze the content according to the indicative ingredients of the Chinese herbal medicine patch.

Figure 8:
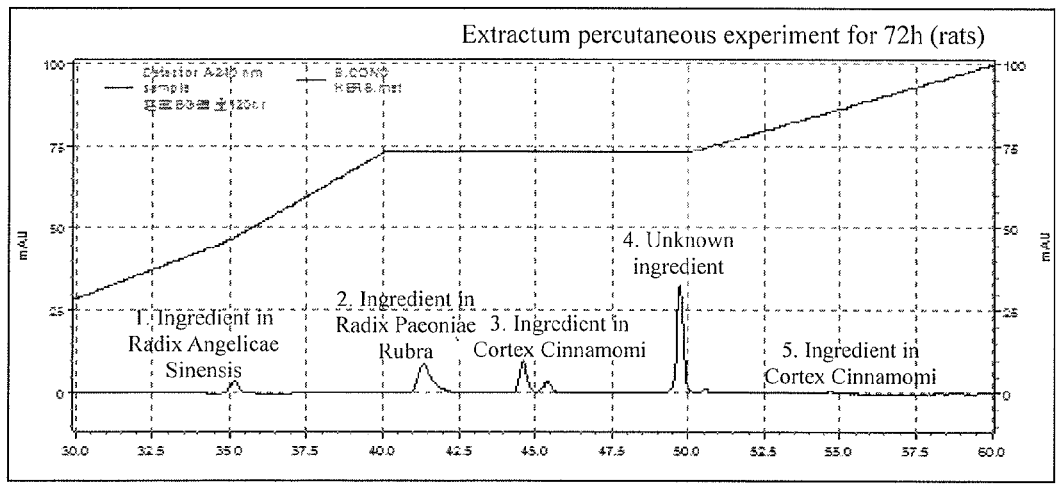
FIG. 8 is a diagram of HPLC results for the percutaneous experiment of extractum having the medicinal material ingredients according to the present invention.

The result is that, percutaneous ingredients that can be detected by HPLC is the following medicinal materials ingredients such as Radix Angelicae Sinensis, Paeonia Lactiflora and Cortex Cinnamomi and so on, which contains the above three indicative ingredients. The HPLC fingerprint is shown in FIG. 8.

Test Example 6

Analgesic Experiment of the Chinese Herbal Medicine Patch in the Present Invention (1) Mice Acetic Acid Writhing Test Method Principle: if the animals are stimulated by chemical substances, for example, apply acetic acid, bradykinin or $K^+$ etc. by intraperitoneal injection to stimulate peritoneum or contact skin, in order to induce pain reaction in the chemical sensitivity acceptor, and show writhing behaviors such as abdomen shrinkage invagination, hind limb extension, body torsion or worming and so on.

Test animals are ICR mice (male, 6-8 weeks). During the experiment, test animals can eat and drink freely. Before the experiment, animals should fast for 24 h. Experiment is divided into three groups, which are respectively negative control group (patch containing no medicine), positive control group (commercial Indomethacin or Diclofenac sodium patch) and experiment group (using 4 different dosages of patch for the experiment), 12 mice in each group.

Figure 9:
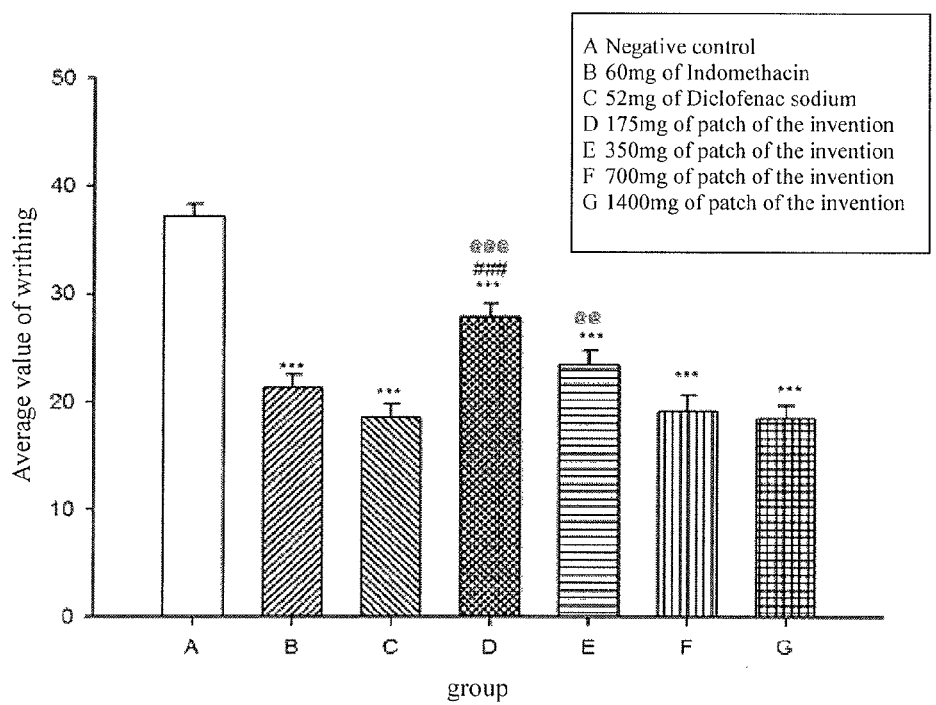
FIG. 9 shows average value of writhing determined by mice acetic acid writhing test.

The mice are weighed and made numbers, then fixed the limbs to the flat plate and shaved off the belly hair. The patch (2 cm×3 cm) is adhered to the belly of mice for 3 h, then removed off (or do not remove the patch). The mice are injected with 0.6 wt % of acetic acid by intraperitoneal injection. The writhing time of mice is observed in 10 minutes and recorded the average value of writhing, the result is shown in FIG. 9.

The result is that, the average value of writhing for the Chinese herbal medicine patch in the present invention is lower than that of the negative control group (patch containing no medicine); therefore, the Chinese herbal medicine patch in the present invention definitely has analgesic effect.

(2) Formalin Test Method

Principle: pain raction of central and peripheral nervous system can be observed in the rats and house mice applied with diluted formalin by subcutaneous injection, and Formalin licking feet experiment is set up early in 1977 by Dubuisson and Dennis, the experiment is a kind of effective and reliable model for the selection of most of analgesic drugs. If people is applied with formalin by subcutaneous injection, formalin can cause strong and acute burning sensation after 4-5 minutes, in the following 30-60 minutes, continuous pain occurs. If house mice are applied with formalin, they may lick their feet or stamp their feet because feet is stimulated by formalin to produce pain, the licking feet time taken by initial pain caused by the injected formalin in 0-5 minutes is called early stage, pain reaction is mainly caused by substance P and bradykinin released through directly irritating pain reaction acceptor. The licking feet time consumed in 15-40 minutes is called later stage, which is mainly caused by some chemical transmitters such as histamine, serotonin, prostaglandin and kinin etc., released from the damaged cells due to inflammatory reaction. In all, licking feet behavior caused by pain of white mice induced by formalin, can evaluate effectively activity and mechanism of analgesic treating inflammatory and noninflammatory pain. Additionally, pain reaction caused by formalin, concentration of which is an important factor. When the concentration of formalin is in the range of 0.02-0.2 wt %, it can only induce licking feet reaction in early stage, identified by optical microscope, and the change is slight, when the concentration of formalin is 1 wt % or more, it can induce licking feet reaction in early stage and later stage, when the concentration of formalin is 5 wt %, acute inflammatory reaction, damage and swelling of granulocytes can be seen from histological identification after 30 minutes.

Test animals are ICR white mice (male, 6-8 weeks). During the experiment, test animals can eat and drink freely. Before the experiment, animals should fast for 24 h. Experiment is divided into three groups, which are respectively negative control group (patch containing no medicine), positive control group (commercial Indomethacin or Diclofenac sodium patch) and experiment group (using 4 different dosages of patch for the experiment), 12 mice in each group.

Figure 10:
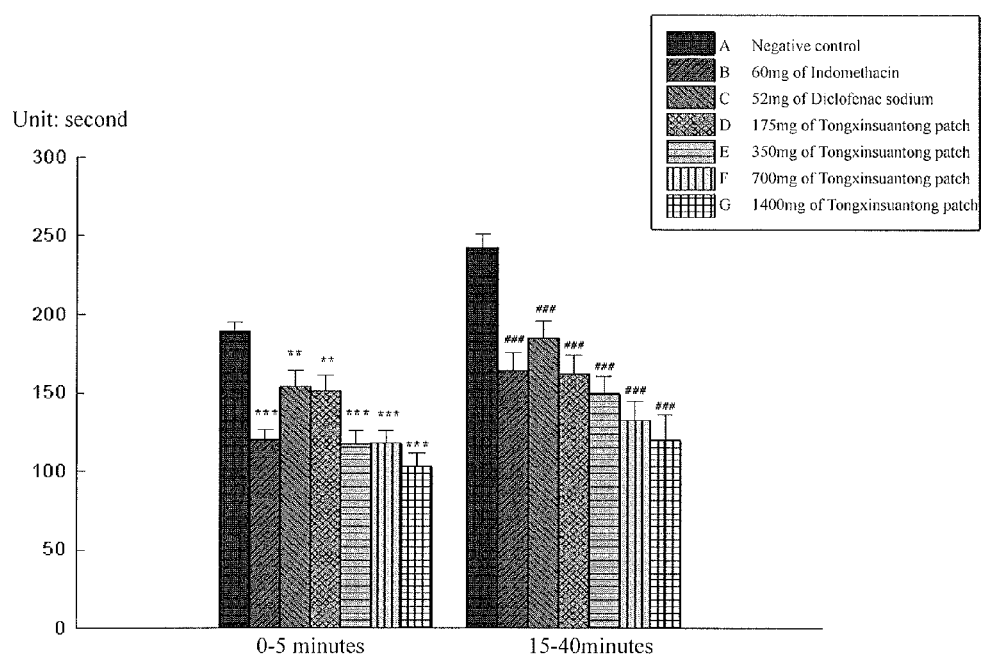
FIG. 10 shows licking feet time determined by mice Formalin test.

The white mice are weighed and made numbers. The patch (2 cm×3 cm) is cut into four equal parts, then adhered to the instep of mice, and then fixed with breathable tape. The patch is removed after 3 h, and the mice are applied with 20 μL of 1 wt % freshly formalin solution on instep by subcutaneous injection. The licking feet time during 0-5 minutes and 15-40 minutes is calculated, and the result is shown in FIG. 10.

The result is that, licking feet time for the Chinese herbal medicine patch in the present invention is lower than that of the negative control group (patch containing no medicine); therefore, the Chinese herbal medicine patch in the present invention definitely has analgesic effect.

Test Example 7

Antiinflammation and Detumescence Test on the Chinese Herbal Medicine Patch in the Present Invention Principle: edema caused by injecting γ-carrageenin into plantar is a biphasic effect, after injected with γ-carrageenin, different substances can be released to induce inflammation and swelling in different time period, that is to say, histamine, serotonin and platelet activating factor (PAF) can be released in the time period of 0-1.5 h or 20 minutes to 1 h (the first stage), and kinin can be released in the time period of 1.5-2.5 h (the second stage), then prostaglandin and leukotriene can be released after 2.5 h (the third stage), leading to inflammation and swelling.

Test animals are SD white rats (male, 6-8 weeks). During the experiment, test animals can eat and drink freely. Before the experiment, animals should fast for 24 h. Experiment is divided into three groups, which are respectively negative control group (patch containing no medicine), positive control group (commercial Indomethacin or Diclofenac sodium patch) and experiment group (using 4 different dosages of patch for the experiment), 8 rats in each group.

Figure 11:
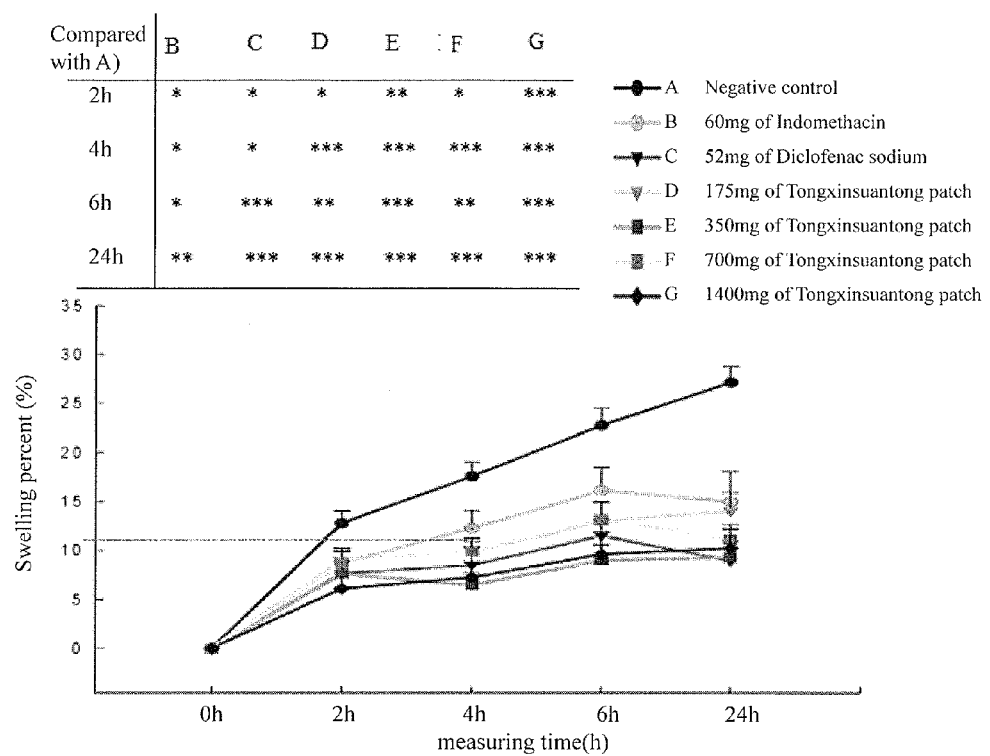
FIG. 11 shows results of antiinflammation, detumescence and acesodyne test for the Chinese herbal medicine patch according to the present invention.

The white rats are weighed and made numbers, drawn a measuring line on the plantar of white rats with sighing pen. The volume of the plantar is firstly measured by a swelling tester. The white rats are dresses with corset elastic bandage to avoid the Chinese herbal medicine patch bited by the white rats. of the white rats in each group are applied with 0.1 mL of Carrageenan (10 mg/mL in saline) by subcutaneous injection in plantar. The Chinese herbal medicine patch (2 cm×3 cm) are adhered to the plantar for positive control group and experiment group, and fixed with breathable tape, swelling percent is measured in the time of 0 h, 2 h, 4 h, 6 h and 24 h with a swelling tester (changing the Chinese herbal medicine patch after determining in different time). Observing the swelling condition in different time and draw swelling curve of experiment group and comparison group, identifying if it is of biometrical differences, as shown in FIG. 11.

The result is that, swelling percent for the Chinese herbal medicine patch in the present invention is lower than negative control group (patch containing no medicine); therefore, the Chinese herbal medicine patch in the present invention definitely has antiinflammation and detumescence effect.

Although the present invention has described the above examples, these examples do not use to define the present invention, a person skill in the art with common knowledge of this field can make various changes and modification without departing from the spirit of the present invention. Thus, the protection scope of the present invention should be that defined by the claims.

What is claimed is:

1. A Chinese herbal medicine composition, comprising:
    a first type medicinal material comprising Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei; and
    a second type medicinal material comprising at least one selected from the group consisting of *Zingiber Officinale, Olibanum, Myrrha*, and combinations thereof, wherein
    the Chinese herbal medicine composition is substantially free of Radix Aconiti, Momordica Cochinchinensis, and Radix Aconiti Kusnezoffii.

2. The Chinese herbal medicine composition according to claim 1, wherein
    the second type medicinal material comprises one selected from the group consisting of *Zingiber Officinale, Olibanum*, and *Myrrha*,
    the Chinese herbal medicine composition contains a total of 11 kinds of medicinal materials, and
    percent by weight of each of the medicinal materials is in a range of 9.09%±5%.

3. The Chinese herbal medicine composition according to claim 1, wherein
    the second type medicinal material comprises two selected from the group consisting of *Zingiber Officinale, Olibanum*, and *Myrrha*,
    the Chinese herbal medicine composition contains a total of 12 kinds of medicinal materials, and
    percent by weight of each of the medicinal materials is in the range of 8.33%±5%.

4. The Chinese herbal medicine composition according to claim 1, wherein
    the second type medicinal material comprises *Zingiber Officinale, Olibanum*, and *Myrrha*,
    the Chinese herbal medicine composition contains a total of 13 kinds of medicinal materials, and
    percent by weight of each of the medicinal materials is in the range of 7.69%±5%.

5. A method for preparing a Chinese herbal medicine exactive comprising the following steps: providing a first type medicinal materials and a second type medicinal materials, wherein the first type medicinal materials include Rhizoma Bletillae, Cortex Cinnamomi, Radix Angelicae Formosanae, Radix Angelicae Sinensis, Paeonia Lactiflora, Rhizoma Notopterygii, Radix Linderae, Glycyrrhizae, Radix Angelicae Pubescentis, and Radix Et Rhizoma Rhei, which are basic medicinal materials, and the second type medicinal materials is one, two or three selected from the group consisting of *Zingiber Officinale, Olibanum* and *Myrrha*, which are added medicinal materials; adding the first type medicinal materials and the second type medicinal materials into the container with organic solvent, making the percent by weight of the first type medicinal materials and second type medicinal materials with the organic solvent reach 1:N, so as to form a first mixed solution, N is a number between 3 and 12; heating the first mixed solution to a first predetermined temperature and performing the extraction for a first predetermined time, so as to carry out first extraction; and filtering the first mixed solution while hot, to achieve filtrate from the first extraction.

6. The method according to claim 5, further comprising the step of: condensing the filtrate from the first extraction into an extractum with a water content of 10-40% by weight and a content of the organic solvent of 3-30% by weight.

7. The method according to claim 6, wherein the water content is 10-20% by weight, the content of the organic solvent is 5-10% by weight.

8. The method according to claim 7, further comprising the following steps: reserving residue from the first extraction; adding the organic solvent again, making the percent by weight of the medicinal materials with the organic solvent be 1:N, so as to form second mixed solution, N is a number between 3 and 12; heating the second mixed solution to a second predetermined temperature and performing second extraction for a second predetermined time, so as to carry out second extraction; and filtering the second mixed solution while hot, to achieve filtrate of the second extraction.

9. The method according to claim 8, further comprising the following steps: mixing the filtrate of the first extraction and the filtrate of the second extraction, and condensing the mixed filtrate into an extractum with a water content of 10-40% by weight and a content of the organic solvent of 3-30% by weight.

10. The preparation method according to claim 5, wherein the first predetermined temperature is between 30° C. and 100° C.

11. The preparation method according to claim 10, wherein the first predetermined temperature is within the range of boiling point of the organic solvent±5° C.

12. The preparation method according to claim 11, wherein the organic solvent is ethanol.

13. The preparation method according to claim 5, wherein the first predetermined time is between 1 h and 6 h.

14. The preparation method according to claim 8, wherein the second predetermined temperature is between 30° C. and 100° C.

15. The preparation method according to claim 8, wherein the second predetermined temperature is within the range of boiling point of the organic solvent±5° C.

16. The preparation method according to claim 15, wherein the organic solvent is ethanol.

* * * * *